(12) United States Patent
Bennett et al.

(10) Patent No.: US 6,233,472 B1
(45) Date of Patent: May 15, 2001

(54) ELECTRODE ASSEMBLY AND METHOD FOR SIGNALING A MONITOR

(75) Inventors: Henry L. Bennett, Chatham, NJ (US); Jeffrey R. Cram, Nevada City, CA (US); Bruce Jay Simon, Mountain Lakes, NJ (US)

(73) Assignee: Patient Comfort, L.L.C., NJ (US)

( * ) Notice: Subject to any disclaimer, the term of this patent is extended or adjusted under 35 U.S.C. 154(b) by 0 days.

(21) Appl. No.: 09/107,098

(22) Filed: Jun. 29, 1998

Related U.S. Application Data

(63) Continuation-in-part of application No. 08/475,024, filed on Jun. 6, 1995, now Pat. No. 5,772,591.

(51) Int. Cl.$^7$ .................................................. A61B 5/0492
(52) U.S. Cl. .......................... 600/383; 600/546; 600/554; 600/557; 607/47; 607/62; 607/139
(58) Field of Search ...................................... 600/383, 546, 600/554, 557, 26; 607/46, 47, 62, 63, 139, 140, 141; 128/898

(56) References Cited

U.S. PATENT DOCUMENTS

| | | |
|---|---|---|
| 2,902,030 | 9/1959 | Kennedy et al. . |
| 3,572,322 | 3/1971 | Wade . |
| 3,774,593 | 11/1973 | Hakata et al. . |

FOREIGN PATENT DOCUMENTS

| | | |
|---|---|---|
| 2113846 | 8/1983 | (GB) . |

OTHER PUBLICATIONS

Ritchie, G., et al., A Microcomputer Based Controller for Neuromuscular Block During Surgery, *Annals of Biomed. Eng* . 13:3–15 (1985).

Edmonds, H.L., et al., Quantitative Surface Electromyography in Anesthesia and Critical Care, *Int J. Clin. Monitoring and Computing* 3:135–145 (1986).

Chang, T., et al., Continuous Electomyography for Monitoring Depth of Anesthesia, *Anesth Analg* . 67:521–5 (1988).

Edmonds, H.L., et al, Objective Assessment of Opioid Action by Facial Muscle Surface Electromyography (SEMG), *Prog. Neuro–Psychopharmacol. & Biol. Psychait* . 12:727–738 (1988).

Paloheimo, et al.: Comparison of Upper Facial and Hypothenar Block, *J. of Clinical Monitoring* 4:256–2600 (1988).

Tammisto, T., et al., Assessment of Neuromuscular Block: Comparison of Three Clinical Methods and Evoked Electromyography, *Eur. J. Anaesthesiol* . 5:1–8 (1988).

Nielsen, T.A., et al., Effects of Dream Reflection on Waking Affect: Awareness of Feelings, Rorschach Movement, and Facial EMG, *Sleep* 12 (3):277–286 (1989).

(List continued on next page.)

*Primary Examiner*—Linda C. M. Dvorak
*Assistant Examiner*—David M. Ruddy
(74) *Attorney, Agent, or Firm*—Bernhard Kreten

(57) ABSTRACT

An electrode assembly adapted to be attached to the skin over selected facial muscle groups picks up signals to be analyzed by an anesthesia adequacy monitor that measures the level of awareness of a living animal, typically a human being. The electrode assembly also includes a stimulator that stimulates a facial nerve to determine the level of paralysis, or neuro muscular block, of the facial muscles. Also disclosed is a method of manufacturing the electrode assembly by printing a pattern of electrically conductive material through a silk-screen or an ink type process onto a flexible layer, and then coating the result with a non-conducting adhesive except at points corresponding to sensing points for the desired muscle groups. Finally, a method for using such sensing and stimulating devices is shown in determining and maintaining an appropriate level of patient awareness, muscle paralysis, and analgesia under anesthesia.

100 Claims, 13 Drawing Sheets

U.S. PATENT DOCUMENTS

| | | |
|---|---|---|
| 3,946,723 | 3/1976 | Servos . |
| 4,082,087 | 4/1978 | Howson . |
| 4,291,705 * | 9/1981 | Severinghaus et al. ............. 600/546 |
| 4,353,372 | 10/1982 | Ayer . |
| 4,359,724 * | 11/1982 | Zimmerman et al. ............... 340/575 |
| 4,448,203 | 5/1984 | Williamson et al. . |
| 4,576,184 * | 3/1986 | Westerman ........................... 128/733 |
| 4,583,549 | 4/1986 | Manoli . |
| 4,763,660 | 8/1988 | Kroll et al. . |
| 4,817,628 * | 4/1989 | Zealear et al. ....................... 128/741 |
| 5,195,531 | 3/1993 | Bennett . |
| 5,817,030 * | 10/1998 | Tarjan et al. ......................... 600/546 |
| 5,906,208 * | 5/1999 | Ishikawa et al. .................... 128/898 |
| 5,957,860 * | 9/1999 | Olive .................................... 600/546 |

OTHER PUBLICATIONS

Paloheimo, M. Assessment of Anaesthetic Adequacy with Upper Facial and Abdominal Wall EMG, *Eur. J. Anaesthiol* . 6:111–119 (1989).

Schwilden, H., Surveillance et Conduite de l'Anesthesie a l'Aide de l'EEG, des Potentiels Evoques, de l'EMG du Muscle Frontal ou du Monitorage de la Contractilite Oesophagienne, *Ann. Fr. Anesth. Reanim* . 8:162–166 (1989).

McAdams, E.T., et al., Designing Biosignal Monitoring Sensors, *Sensors*, :25–27 (1994).

Datex–Engstrom, NeuroMuscular Transmission Module Product Description, Internet Web Page (1998) (reporting prior art NMBM device by Datex–Engstrom discussed above).

\* cited by examiner

PROVIDING ELECTRODE ASSEMBLY

ELECTRODE ASSEMBLY AND METHOD FOR SIGNALING A MONITOR

RELATED APPLICATION

This application is a continuation-in-part of U.S. patent application Ser. No. 08/475,024, filed Jun. 6, 1995, now U.S. Pat. No. 5,772,591, issued Jun. 30, 1998.

FIELD OF THE INVENTION

The following invention relates to devices which are used in the field of assessment of consciousness of a person, electromyography, and specifically for measuring the clinical condition of a patient under anesthesia by noting the muscular activity related to facial micro-expressions. This invention is also concerned with a method for determining the adequacy of anesthesia, and the level of paralysis therefrom, during surgery and otherwise through stimulating and measuring the muscular activity of the face. This method and this device allows for quick application of stimulating and multiple sensing means for the different muscles in the face.

INCORPORATION OF SPECIFICATION BY REFERENCE

U.S. Pat. No. 5,195,531 describing an anesthesia adequacy monitor and method, was issued to Henry L. Bennett on March 23, 1993. The disclosure of U.S. Pat. No. 5,195,531 (the "First Bennett Patent") is specifically incorporated herein by reference.

BACKGROUND OF THE INVENTION

In the past, when the face was stimulated and monitored for facial expressions to indicate the depth of anesthesia, individual electrodes were often applied one at a time. The time required to apply individual electrodes was significant, especially when a full surgical operating crew was standing by or there were patients waiting for their turn in the surgery operating theater.

Additionally, when individual electrodes are used, there was the problem of multiple wires leading from the patient to any type of signal receiving device. It was, of course, important to keep track of which wire was connected to which electrode and where that electrode was placed on the face or other part of the patient's body. It was also important that the wires be hooked into the proper receptacle in any type of monitor. Again, valuable time was taken up in order to assure that the wires and electrodes had been properly placed on the patient and into the monitoring device.

In addition, as noted in the Background Of The Invention of the First Bennett Patent, there has been no expeditious method of monitoring the depth of unconsciousness of a patient under anesthesia. In this regard, anesthesia often seeks to provide a variety of results for the patient during surgery and invasive medical procedures. One such result is to provide oblivion through a state of unconsciousness. Another is to provide freedom from pain registration, conscious or unconscious. In seeking to achieve oblivion for the patient, however, the anesthesia can and often does paralyze muscle groups in varying degrees from partial paralysis to total paralysis.

In addition to the issues explained about the prior devices and methods explained in the First Bennett Patent, the surface electromyogram devices identified therein did not sense a sufficient number of facial muscle groups to procure sufficient response data. Similarly, they also have not provided a mechanism to readily assess the level of paralysis (neuro muscular blockade) of facial muscle groups brought about by anesthesia and to then quickly process this type of information in order to yield more accurate indicators of the depth of paralysis of the person, if any, and also of the depth of unconsciousness of a person in view of paralysis, if any.

As also shown in the prior art cited in the First Bennett Patent and in this specification, there are many electromyogram devices in the prior art for monitoring neuro muscular blockade during anesthesia ("NMBMs"). Another example of an NMBM is the Datex-Engstrom NeuroMuscular Transmission Module, M-NMT. This NMBM utilizes two stimulator electrodes secured to a patient's wrist, a return electrode secured to the patient's finger, and a sensor mounted on the patient's thumb to monitor the hypothenar muscle stimulated by the ulnar nerve. This NMBM is not designed for easily and reliably mounting on and sensing facial muscle groups and does not include any means of receiving output from the sensors, calculating and reporting consciousness indicators based on the output from the sensors, and also quickly and automatically processing neuro muscular blockade information to more accurately and automatically measure the depth of paralysis, if any, and the depth of consciousness of a person.

The following disclosures reflect the state of the art of which applicant is aware and is included herewith to discharge applicant's acknowledged duty to disclose relevant information available. It is stipulated, however, that none of these references teach singly nor render obvious when considered in any conceivable combination the nexus of the instant invention as disclosed in greater detail hereinafter and as particularly claimed.

| U.S. PAT. NO. | ISSUE DATE | INVENTOR |
| --- | --- | --- |
| 2,902,030 | September 1, 1959 | Kennedy et al. |
| 3,572,322 | March 23, 1971 | Wade |
| 3,774,593 | November 27, 1973 | Hakata et al. |
| 3,946,723 | March 30, 1976 | Servos |
| 4,082,087 | April 4, 1978 | Howson |
| 4,353,372 | October 12, 1982 | Ayer |
| 4,448,203 | May 15, 1984 | Williamson et al. |
| 4,583,549 | April 22, 1986 | Manoli |
| 4,763,660 | August 16, 1988 | Kroll, et al. |
| 5,195,531 | March 23, 1993 | Bennett |
| FOREIGN PATENT DOCUMENTS | | |
| GB2, 113,846 | August 10, 1983 | Rantala, B., et al. |

OTHER PRIOR ART

Including Author, Title, Date, Pertinent Pages. Etc.

Ritchie, G., et al., A Microcomputer Based Controller for Neuromuscular Block During Surgery, *Annals of Biomed. Eng.* 13:3–15 (1985)

Edmonds, H. L., et al., Quantitative Surface Electromyography in Anesthesia and Critical Care, *Int. J. Clin. Monitoring and Computing* 3:135–145 (1986)

Chang, T., et al., Continuous Electromyography for Monitoring Depth of Anesthesia, *Anesth Analg.* 67:521–5 (1988)

Edmonds, H. L., et al., Objective Assessment of Opioid Action by Facial Muscle Surface Electromyography (SEMG), *Prog. Neuro-Psychopharmacol. & Biol. Psychiat.* 12:727–738 (1988)

Paloheimo, et al.: Comparison of Upper Facial and Hypothenar Block, *J. of Clinical Monitoring* 4:256–260 (1988)

Tammisto, T., et al., Assessment of Neuromuscular Block: Comparison of Three Clinical Methods and Evoked Electromyography, *Eur. J. Anaesthesiol.* 5:1–8 (1988)

Nielsen, T. A., et al., Effects of Dream Reflection on Waking Affect: Awareness of Feelings, Rorschach Movement, and Facial EMG, *Sleep* 12 (3):277–286 (1989)

Paloheimo, M., Assessment of Anaesthetic Adequacy with Upper Facial and Abdominal Wall EMG, *Eur. J. Anaesthiol.* 6:111–119 (1989)

Schwilden, H., Surveillance et Conduite de l'Anesthesie a l'Aide de l'EEG, des Potentiels Evoques, de l'EMG du Muscle Frontal ou du Monitorage de la Contractilite Oesophagienne, *Ann. Fr. Anesth. Reanim.* 8:162–166 (1989)

McAdams, E. T., et al., Designing Biosignal Monitoring Sensors, *Sensors,* :25–27 (1994)

Datex-Engstrom, NeuroMuscular Transmission Module Product Description, Internet Web Page (1998) (reporting prior art NMBM device by Datex-Engstrom discussed above)

The Kennedy et al. patent, U.S. Pat. No. 2,902,030, described the electrodes at the bottom of column 3 as "small discs of sponge rubber wetted with saline solution or small metal disc attached to the surface of skin with adhesive tape." A good contact was provided by application of a small amount of "electrode jelly" between the skin and a metal electrode. The electrodes were applied in the supra orbital region of the head of a person. No specific facial muscle group was mentioned.

The Servos patent, U.S. Pat. No. 3,946,723, disclosed attaching a pair of electrodes to opposite temples of a patient for detecting horizontal eyeball movements using the cornea-retina potential. A second pair of electrodes attached to brow and cheek bones detected, at a different time, the cornea-retina potential showing vertical eye movement. Finally, a ground electrode was attached elsewhere on the face. The data gained was used to diagnose the presence of nystagmus as an indicator of vestibular disorders. A patient under anesthesia may not have had reliable eye movements or even any purposeful eye movements at all.

The patent Williamson, et al., U.S. Pat. No. 4,448,203 taught the use of a device for sensing electrical activity within target muscles such as the masticatory muscle. One part of the device shown was a pad with two electrodes disposed on one side and a grounding electrode disposed on the other side. The method of use for this device was for the patient to hold the electrode pad up against his face with the two electrodes sides contacting the face and the one electrode side contacting the finger of the holder. Because the patient must hold the electrode device against his face, this device was impractical for a patient under anesthesia.

The patent to Manoli, U.S. Pat. No. 4,583,549, disclosed a pad with either three or six electrodes placed in a fixed precordial configuration to assist in obtaining an ECG displaying electrical activity of the cardiac musculature. The electrodes used were either silver plated copper discs with silver/silver chloride eyelets attached to provide a convenient hook-up point for ECG recording cables, or copper discs and copper connecting paths to connector edge tab which are etched on the flexible printed circuit board (with conductive gel coated on the discs and the rest of the board coated with a non conductive adhesive and release paper). Problems remained with the manufacture of the second described electrodes because of the care necessary to assure that the conducting gel coated only the discs, that the insulating coat necessary to avoid contact between the circuits and the patient's skin was completely protective, and the necessity of hooking the six conductor cable to the connector edge tab.

The patent to Rantala taught the use of a device for measuring the depth of anesthesia which combined a surface electromyogram attached to a facial muscle with an electroencephalogram and an electromyogram attached to a patient's hand. While this application did sense the facial muscle activity, it interpreted the activity directly rather than using surface electromyogram readings to determine a facial expression corresponding to the consciousness of the patient, as does the applicant's device. Furthermore, the applicant's device uses an array of surface electromyograms providing a more accurate representation of a patient's facial expression, and hence a more accurate representation of the patient's awareness level.

The article by Ritchie, et al. in the Annals of Biomedical Engineering, 1985 described the placement of stimulating and recording electrodes on the wrist and palm of the patient. The electrodes were described as 30-gauge needles that were subcutaneously inserted near the ulnar nerve. The recording electrodes were infant EKG surface electrodes.

The article by Edmonds, et al. published in 1986 in the International Journal of Clinical Monitoring and Computing described attaching adhesive skin electrodes over the belly of the frontalis muscle and also electrodes over the temporal bone and mastoid process. This was done for the purpose of determining the level of a patient's awareness. In a later article by Edmonds, e al. in 1988 in the Prog. Neuro-Psychopharmacol. & Biol. Psychiat. an electrode was placed over the same belly of the medial frontalis muscle with a reference electrode placed over the mastoid process. Again, no more than one muscle group appears to have been attached to one individual electrode.

The article by Chang is of interest in that it also used a surface electromyogram attached to a facial muscle group and electroencephalogram data during surgery. However, the method taught in this article was designed to effectively administer anesthesia and provided no method for monitoring the awareness level of the patient for patient comfort as does the instant invention.

The article by Nielsen disclosed using electrode pairs with an interelectrode distance of 2 cm. center to center. Facial sites selected for evaluating REM sleep were right and left corrugator superclli (for sadness brow-knitting motion) and right and left zygomaticus major (for happiness smiling). The readings were used to judge feeling-specific motor activity during imagery reflection of REM sleep, not awareness during anesthesia.

The article by Paloheimo in the 1988 *Eur. J. Anaesthiol,* told of using surface electrodes in pairs to record facial electromyographic activity. The first pair was attached on the forehead 3 cm above the mid-eyebrow and on the mastoid process, with a ground electrode on the temporal area. A second pair was located on the mamillary end anterior axillary lines 10 cm. apart within the left dermatomes, with a ground electrode on the external iliac process. No assembly of electrodes to save applying electrodes one at a time was discussed.

The second article by Paloheimo in the *J. of Clinical Monitoring* described attaching one pair of recording electrodes in the midline of the forehead and above the mid portion of an eyebrow for recording electrically evoked muscle potentials. Stimulation was provided by attaching a different pair of stimulating electrodes, one just posterior to the lower part of the pinna and the other just anterior to the tragus. The facial muscle stimulated were procerus, frontalis, corrugator, and orbicularis oculi muscles. No mention was made of recording the patient's unstimulated state.

The article by McAdams, et al. published in 1994 discussed how flexible substrates have been printed with thin layers of silver loaded ink to serve as electrodes. Also discussed was how a tab of a conductive sensor extended beyond the portion of an electrode coated with a solid, conductive adhesive hydrogel and was adapted to be connected to a monitor cable with an alligator clip. However an assembly having more than one electrode was not discussed.

The device and method of this application more effectively achieves the purpose of providing for quick and sure attachment of electrodes to the tissue of a living animal, especially the face of a human patient undergoing surgery. The electrode assembly can, when serving as the sensing means for picking up signals through the skin of facial muscle groups, provide an anesthesiologist with a reliable indicator of the patient's awareness level when the patient is otherwise uncommunicative. One particularly preferred embodiment of the assembly has sensors for picking up signals of five different facial muscles and further includes NMBM stimulators and sensors to reliably and more easily monitor neuro muscular blockage (paralysis) of the patient.

The device and method of this application also more easily, readily, economically, and effectively senses one or more facial muscle groups, assesses the level of paralysis of facial muscle groups, processes the paralysis information in order to promptly indicate the paralysis level and the depth of unconsciousness of a person in view of paralysis, if any.

SUMMARY OF THE INVENTION

The applicant's preferred device provides a convenient, effective, and economical electrode assembly for monitoring differential electrical states in various parts of a living animal. Preferably, the electrode assembly can be used for simultaneous monitoring of the nerve signals to facial muscle groups to reflect the patient's facial muscle tonus, which can be used as a reliable indicator of the level of awareness for the patient while under anesthesia. In one embodiment, the electrode assembly, especially when it includes at least three electrodes, preferably five electrodes, can be used to monitor the difference between two muscle groups. In yet another embodiment, the electrode assembly includes thirteen electrodes to monitor five muscle groups and stimulate, and monitor the resulting effect on, at least one of the muscle groups.

The preferred electrode assembly has a pattern of electrically conductive material printed on a flexible layer, and also a non-conductive adhesive, which serves to isolate electrodes from each other. The assembly is adapted to follow the facial contours of a patient. Also the electrode assembly, by having a substantially uniform thickness, prevents pressure points from developing when the electrode assembly comes between the living animal tissue and any support surface such as an operating table or bed pillow.

Using the electrode assembly as a sensing means for judging the state of patient awareness, an anesthesiologist can better control and provide greater comfort for a patient undergoing anesthesia during the course of surgery. Specifically, the electrode assembly allows quick and sure attachment and a preconfigured pattern for applying the electrodes over selected facial muscle groups. The design of the electrode, with the trailing ribbon attached to the electrode sensing points in an unbroken electrical pathway, allows a monitor or other signal processing device to receive what the electrodes have picked up. After processing the signals using one or more algorithms, the anesthesiologist may view a display representing the patient's face or other indicators derived from the processed signals. Based upon this information, the anesthesiologist then can control the dosage of anesthetic to reach the desired level of patient awareness, paralysis, and analgesia. These are all done independently with different drugs based on the three signals from FACE—level of a) awareness, b) paralysis, and c) analgesia. Additionally, the signal processor can be informed of artifact generating events which can be subtracted out from the signal received by the processor or monitor. This allows the surgeon to use such devices as an electric cauterizer during the course of surgery without interfering with the anesthesiologist efforts to maintain a desired level of patient awareness.

Fabrication of the electrode assembly can be based upon a silk-screen printing method, but preferably an ink type printing process is used. A flexible layer, which is characterized by resisting linear distortion, is printed with a pattern of electrically conductive material. Over this pattern is placed non-conductive adhesive either in the form of a pre-shaped pad with apertures allowing for contact with the living tissue of the animal through an electrolytic medium, or the pattern of electrically conductive material is coated with a non-conductive adhesive except at points where pads prevent coating and such points correspond to sensing points on the animal. A detachable layer over the electrode area can preserve the electrode assembly during shipping.

In designing the preferred pattern of electrically conductive materials, the locations of the Corrugator and Frontalis muscle groups can be taken into consideration for one set of electrodes and stimulators, as well as the Zygomatic, Orbicularis Oculi, and Masseter facial muscle groups in the case of a second group of electrodes. Finally the ribbon trailing off the area of contact between the electrodes and tissue can be adapted at the opposite end to be engaged by the prongs of a spring-biased signal input clamp, or preferably a mechanical clamping ZIF connector.

The electrode assembly can thus be attached to a processor to process output from the sensing electrodes according to predetermined analysis programs or algorithms. The processor can be attached to a display or other device reporting or utilizing output from the processor in order to monitor the consciousness, paralysis, or analgesia of the person to whom the electrode assembly is attached.

Preferably, the electrode assembly includes stimulators for stimulating the upper branch of the facial nerve and recording the response at the Corrugator facial muscle preferably through the use of non-invasive, interferential stimulation. Upon stimulation, the sensors at the Corrugator facial muscle area indicate the response of that muscle area and thus provide an indication of the level of paralysis, if any (including undesirable total paralysis rendering the facial muscles incapable of micro-movements and the attendant indications awareness or stress information). Partial paralysis information can be used by the processor to adjust paralysis-affected monitoring of the facial muscle sensors, such as monitoring pursuant to sensor summation algorithms to report the awareness of the monitored person. As long as the paralysis is not total, the processor can also apply, and report the outcome of, other methods of analysis, such as sensor differential or ratio algorithms that report the stress or pain registering with the person being monitored.

There are other aspects of the invention that will become apparent as the specification proceeds below.

OBJECTS OF THE INVENTION

Accordingly, it is an object of the present invention to provide a device which allows for quick and accurate placement of electrodes upon the tissue of a living animal to monitor differential electrical states.

Another object of the present invention is to provide an electrode assembly which is easily and economically manufactured by well-known techniques such as silk-screen or ink type printing process.

Another object of the present invention is to provide a sensing means preconfigured to pick up signals from certain facial muscle groups that will serve as a reliable indicator of the level of awareness of a patient undergoing anesthesia wherein the same preconfiguration arrangement of electrodes can be used with different individuals.

A further object is to provide stimulators, preferably of the non-invasive type and mounted within the electrode assembly, for stimulation of a facial nerve and measurement of the responsive movement, if any, of the stimulated facial muscle.

A related object is to have the stimulating and sensing means sense the level of paralysis, of any, of the facial muscles.

Yet another object of the present invention is to provide for an electrode assembly of substantially uniform thickness which assures that when the assembly is in between the patient's tissue and a bed pillow or mattress or surgery table that no pressure points are developed during the monitoring of the patient.

Another object of the present invention is to provide a method for informing an anesthesiologist of the level of patient awareness through the use of an electrode assembly which picks up signals from facial muscle groups which can be processed to provide a display representing the patient's facial muscle tonus, the display can be used by the anesthesiologist to monitor the patient's level of awareness and respond thereto with differing dosages of anesthetic and/or level of analgesia.

Viewed from a first vantage point it is the object of the present invention to provide an electrode assembly for monitoring differential electrical states in various parts of a living animal, comprising: a flexible layer, a pattern of electrically conductive material, disposed upon one side of the flexible layer wherein the pattern contains at least two electrodes and is adapted to be connected to a signal receiving means, and a non-conducting adhesive that electrically isolates at least one electrode from another electrode, but allows at least two electrodes to contact the tissue of the living animal.

Viewed from a second vantage point it is the object of the present invention to provide a method for maintaining an appropriate level of patient awareness under anesthesia, the steps including: providing at least one electrode assembly, comprising a flexible layer, a pattern of electrically conductive material, disposed upon one side of the flexible layer wherein the pattern contains as at least two electrodes and is adapted to be connected to a signal receiving means, a non-conducting adhesive that electrically isolates at least one electrode from another electrode, but allows at least two electrodes to contact the tissue of said patient; and attaching the assembly to the face of the patient, picking up a signal with the electrodes, receiving the signal in a processing device through a signal receiving means, processing the signal received from the electrodes to determine what facial expression the signal represents by comparing the signals from different electrodes, the signals being reflective of the patient's facial muscle tonus, displaying the processed signal for viewing by an anesthesiologist on a display, anesthetizing the patient with an initial dosage of anesthetic to create muscle relaxation in a desired level of awareness, and controlling the patient's level of awareness and analgesia.

Viewed from a third vantage point it is the object of the present invention to provide a sensing means adapted to signal an awareness level detector for informing an anesthesiologist of the level of awareness of a patient under anesthesia through detection of the patient's facial expression comprising, in combination: a flexible layer, a pattern of electrically conductive material, disposed upon one side of the flexible layer wherein the pattern contains as at least two electrodes and is adapted to be connected to a signal receiving means, a non-conducting adhesive that electrically isolates at least one electrode from another electrode, but allows at least two electrodes to contact the face of said patient.

Another object is to provide a device and method that stimulates and senses micro-motion in facial muscles in order to: (i) determine and report the level of paralysis of the muscles; (ii) adjust awareness determining algorithms to continue to adequately report the awareness or consciousness of a person despite partial paralysis; (iii) report the level of pain or stress registering with a person; and (iv) provide information about awareness, paralyzation, and stress or pain so that anesthesia may be more appropriately administered to procure the desired outcome and minimization or elimination of pain, stress, and consciousness of a patient during surgery, for example.

These and other objects of the present invention, such as those set forth in the First Bennett Patent, will be made manifest when considering the following detailed specification when taken in conjunction with the appended drawing figures.

DESCRIPTION OF PREFERRED EMBODIMENTS

Figure 1:
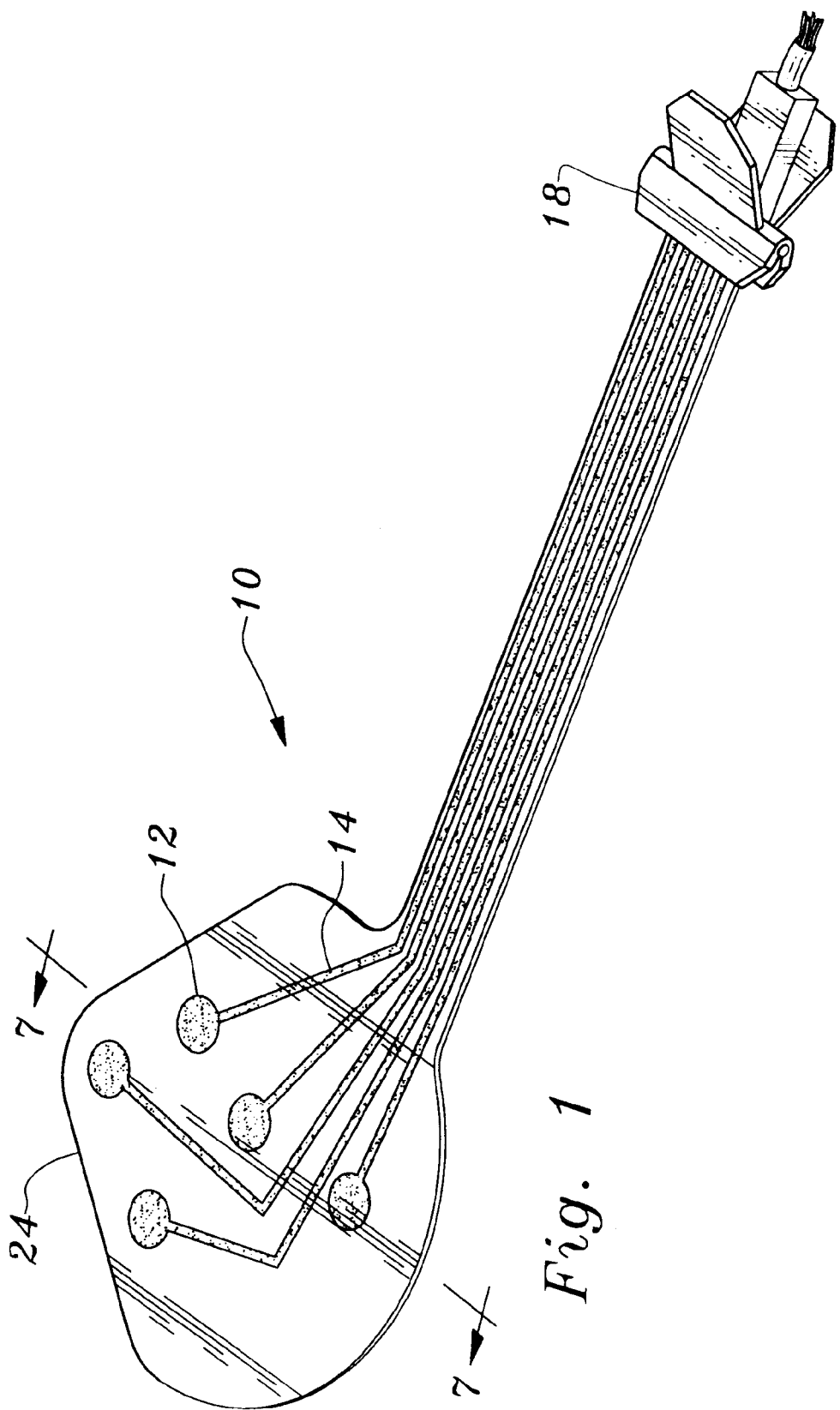
FIG. 1 is a perspective drawing of a two-muscle-area electrode assembly as engaged with a spring biased signal receiving clamp.
Figure 2:
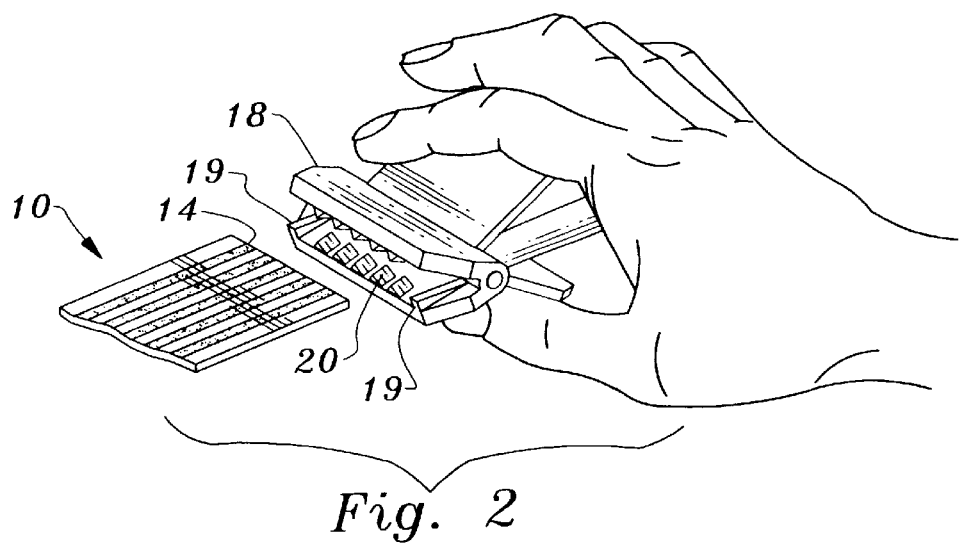
FIG. 2 is a perspective drawing showing the two-muscle electrode assembly being engaged by the spring biased signal receiving clamp.

Considering the drawings, wherein like reference numerals denote like parts throughout the various drawing figures, reference numeral 10 is directed to a two-muscle electrode assembly according to the present invention. Referring now to FIG. 1, an electrode assembly 10 is shown engaged with spring biased signal input clamp 18. Leading from electrode contact points 12 are electrical connecting paths 14 which carry any signal received by electrode contact points 12 to spring biased signal input clamp 18. The electrode contacts points 12 and electrical connecting paths 14 are disposed upon flexible layer 24. Flexible layer 24 can be made from any of a number of flexible plastic substrates. Depending on the type of plastic used, the thickness of the flexible layer can vary from 1 mil to 3 mil, preferably being 2 mil for preferred plastic. A preferred embodiment of electrode assembly 10 uses one type of plastic that is a combination of vinyl and mylar plastics. Going on now to FIG. 2, spring bias signal input clamp 18 is shown with the jaws open ready to receive electrode assembly 10. The ribbon of the electrode is guided into the proper position in the jaws of the clamp 18 by guides 19. Contact points 20 engage individually, each one of the electrical connecting paths 14 because the electrical connecting paths 14 have been spaced apart a proper distance to ensure engagement with only one contact point 20 of spring biased signal input clamp 18. FIG. 1 does not show the electrode assembly in a perspective view of actual use, it is for illustration purposes alone. It is contemplated that the electrode assembly 10 would first be placed upon the living animal tissue, such as a patient's face, before being hooked up to spring biased or ZIF type signal input clamp 18. Of course, it is to be understood that other methods of engagement for electrode assembly 10 could be used to carry the signal picked up by electrode assembly 10 and deliver it to a signal processor.

Figure 3:
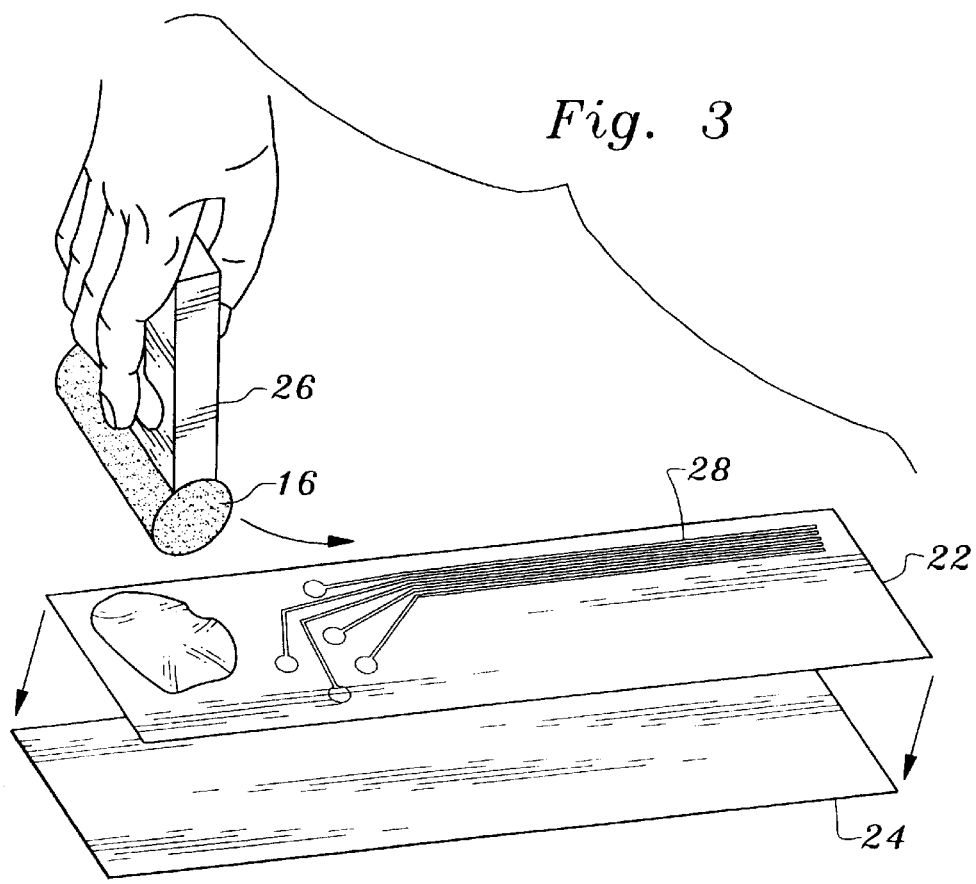
FIG. 3 is a representation of the first step fabricating the two-muscle electrode assembly wherein electrically conductive material is applied to the flexible layer.

Referring now to FIG. 3, the flexible layer 24 is shown as being prepared to receive the electrically conductive material 16 that makes up electrical connecting paths 14 and electrode contact points 12. Electrically conductive material 16 is carried to mask means 22 by squeegee 26. Mask means 22 can be a silk-screen used in a silk-screen printing process or an ink type process. As shown, mask means 22 contains openings 28 that allows electrically conductive material 16 in squeegee 26 to flow through onto flexible layer 24 when mask means 22 is lowered into contact with flexible layer 24.

Figure 4:
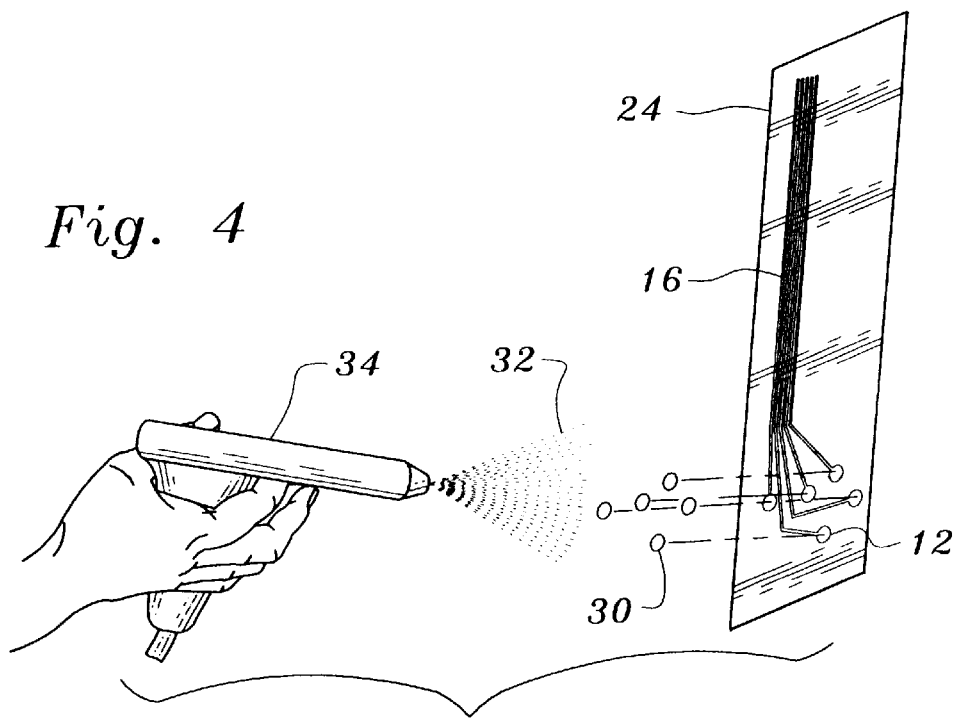
FIG. 4 is the second step in the fabrication of the two-muscle electrode assembly wherein non-conductive adhesive is applied to the result of the fabrication step shown in FIG. 2.

After allowing the electrically conductive material to dry, the flexible layer 24, with a pattern of electrically conductive material 16 displayed thereon one side, can be treated in various ways to complete the fabrication of electrode assembly 10. As shown in FIG. 4, buttons 30 are placed over the electrode contact points 12. Then, non-conductive adhesive 32 is sprayed onto a side of the flexible layer 24 with the pattern of electrically conductive material 16. These buttons 30 are shown as being put into engagement with the electrode contact points 12. The electrode contact points 12 will match up with later locations on the skin of the animal. Typically the locations are placed so that the electrode contact points 12 can pick up signals from the desired muscle groups. Non-conductive material 32 is now applied by spray gun 34 to coat the entire surface of flexible layer 24 including electrically conductive material 16 and buttons 30. After the material has been sprayed on, the buttons 30 do not adhere to the electrode contact points 12. This allows easy removal of any non-conductive material from the area over the electrode contact points 12, especially if a non-conductive material 32 has been scored over the perimeter of electrode contact points 12.

Other methods of applying non-conductive material 32 can include a second silk-screen printing similar to FIG. 3. The non-conductive material 32 is preferably applied using a printing roller without any mask means, as long as buttons 30 are used. However the non-conductive material 32 is applied to flexible layer 24, it is necessary to ensure that the electrically connecting paths 14 and electrode contact points 12 do not come into contact with each other. If allowed to, this could well short out the pathway for delivering the signal received to the processor unit.

Figure 5:
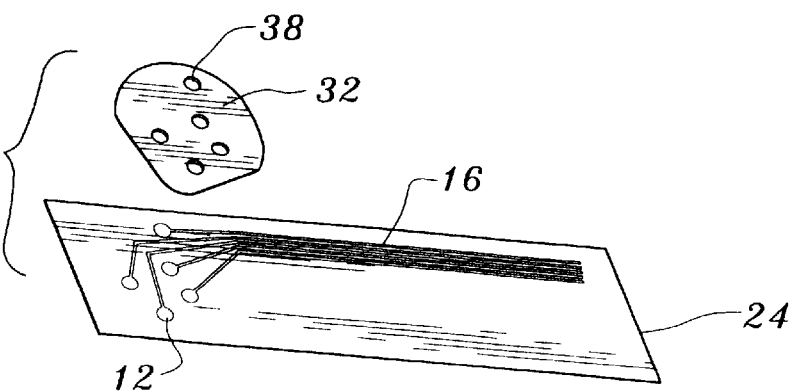
FIG. 5 is a perspective view of an alternate second step wherein a pre-formed shape of non-conductive adhesive is about to be mated with the result of the fabrication step shown in FIG. 2.

Another way to apply the non-conductive material 32 to flexible layer 24 with electrically conductive material disposed on one side is for a pre-formed shape, like a pad, to be placed over the flexible layer 24 with electrically conductive material 16 on one side as shown in FIG. 5. Within this pre-formed layer, at the appropriate spots over the electrode contact points 12, are apertures 38, preferably filled with an electrolytic medium 40 seen later in FIG. 7 such as lanolin based cream containing electrolytes (such as Signa Creme 1705 available from Parker Laboratories). When applied to the tissue of a living animal, the apertures allow signals to be received by electrode contact points 12, especially if an electrolytic medium is used. Because the layer is pre-formed, mating it with the pattern of electrode contact points 12 on flexible layer 24 should not require much micro-adjustment of the location.

Figure 6:
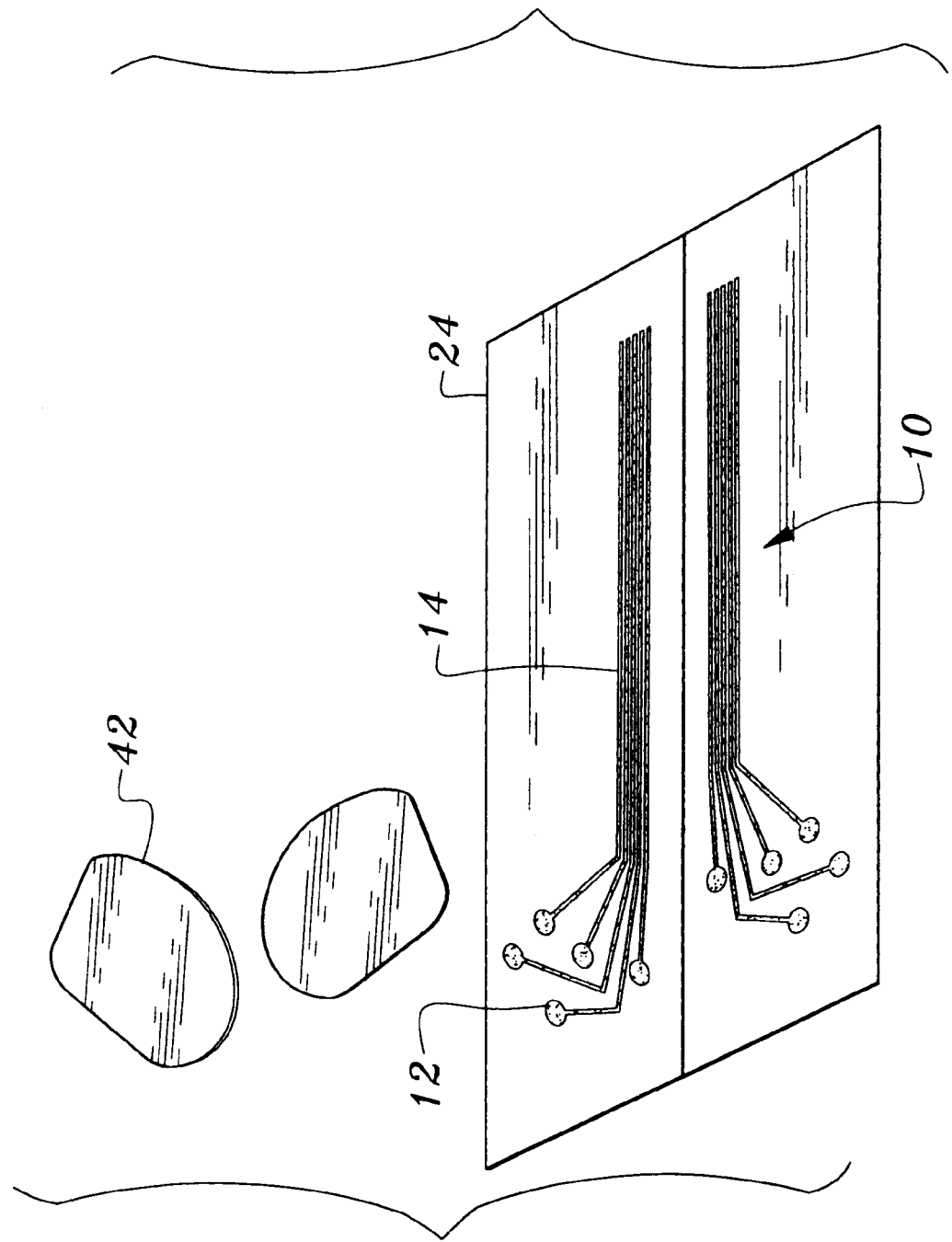
FIG. 6 is a perspective view of the third step in the fabrication process wherein a detachable pad is applied to the result of the second step of the fabrication process.

Referring now to FIG. 6, flexible layer 24 with electrical connecting paths 14 and electrode contact points 12 and non-conductive material 32 applied is ready for mating with detachable pads 42. As can also be seen in FIG. 6, electrode assemblies 10 are often produced in multiple numbers on a single flexible sheet 24. After detachable pads 42 are mated with the electrode assemblies 10, the assemblies 10 can be separated. Separation can be done through use of a knife, scissors, or other appropriate cutting means. As can be observed in FIG. 6, the electrode assemblies are sometimes mirror images of each other. Also, depending upon the muscle groups that the user may wish to monitor, electrode assemblies 10 can assume different configurations for their electrode contact points. Although FIGS. 3, 4 and 5 show only the preparation of a single electrode assembly, the silk-screen mask 22 can have many electrode assembly patterns present and a number of electrode assemblies 10 can be printed onto a flexible layer 24.

Figure 7:
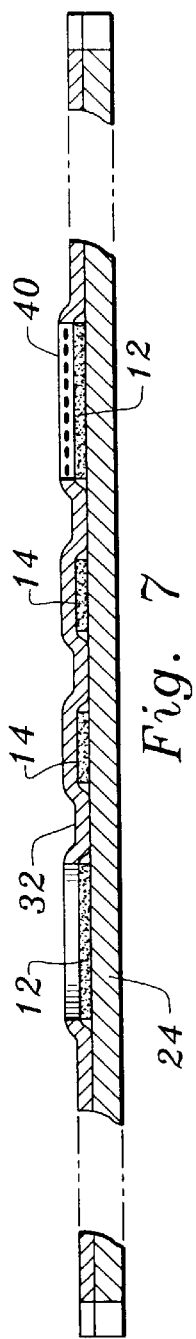
FIG. 7 is a cross section view of the two-muscle electrode assembly taken along line 7—7 of FIG. 1.

Referring now to FIG. 7, the electrode assembly 10 is seen in cross section. Flexible layer 24 accounts for much of the thickness of the assembly 10. Differing electrical connecting paths 14 and the electrode contact points 12 are also present. The space above contact points 12 is vacant, while non-conductive adhesive 32 is above other parts of flexible layer 24. At the far right, the space above contact point 12 is pre-filled with electrolytic medium 40. However, the substantially uniform thickness of electrode assembly 10 is preserved due to the thinness of the non-conductive adhesive 32. Thus, the presence or absence of non-conductive adhesive 32 does not radically change the thickness of electrode assembly 10. Therefore, when electrode assembly 10 is between the tissue of a living animal and a support means, such as an operating tale or a pillow on a bed, then substantially uniform thickness prevents any point from becoming a pressure point. The lack or pressure points in electrode assembly 10 when so used prevents the development of sores and other discomfort for the patient.

Figure 8:
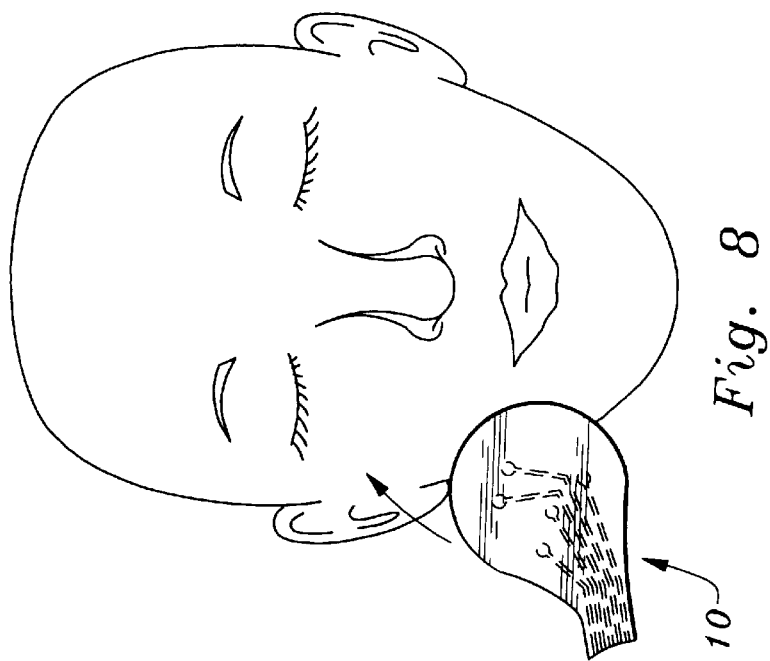
FIG. 8 is a perspective view of the two-muscle electrode assembly being applied to the person's face after application of an electrolytic medium to the electrode contact points.

Referring now to FIG. 8, a patient's face is prepared to receive electrode assembly 10 which has no electrolytic medium packaged with it. It is preferred to use pre-jellied electrodes in large-scale manufacturing. An electrolytic medium 40 such as Signa brand creme, could also be applied to the electrode assembly, if the assembly is not provided with a medium already in contact wells over control points 12. This medium 40 comes in the form of a thick lotion. The medium is preferably thick enough to hold a bead shape in the well of the electrode contact point. Other electrode assemblies 10 can be supplied with the medium in the well, before the detachable pads 42 are mated to the flexible layer 24. Other electrolytic mediums 40 such as electrode paste with adhesive characteristics can be applied to the electrode assembly 10. The skin over the orbicularis oculi 48 muscle group and the zygomatic 50 muscle groups in FIG. 8 is shown as ready to receive the electrode assembly 10. FIG. 8 also shows electrode assembly 10 being positioned to be applied to the patient's face over the muscle groups whose monitoring is desired. In a similar fashion, other muscle groups can have electrolytic medium 40 put into the contact points wells, and then electrode assemblies 10 applied.

Figure 9:
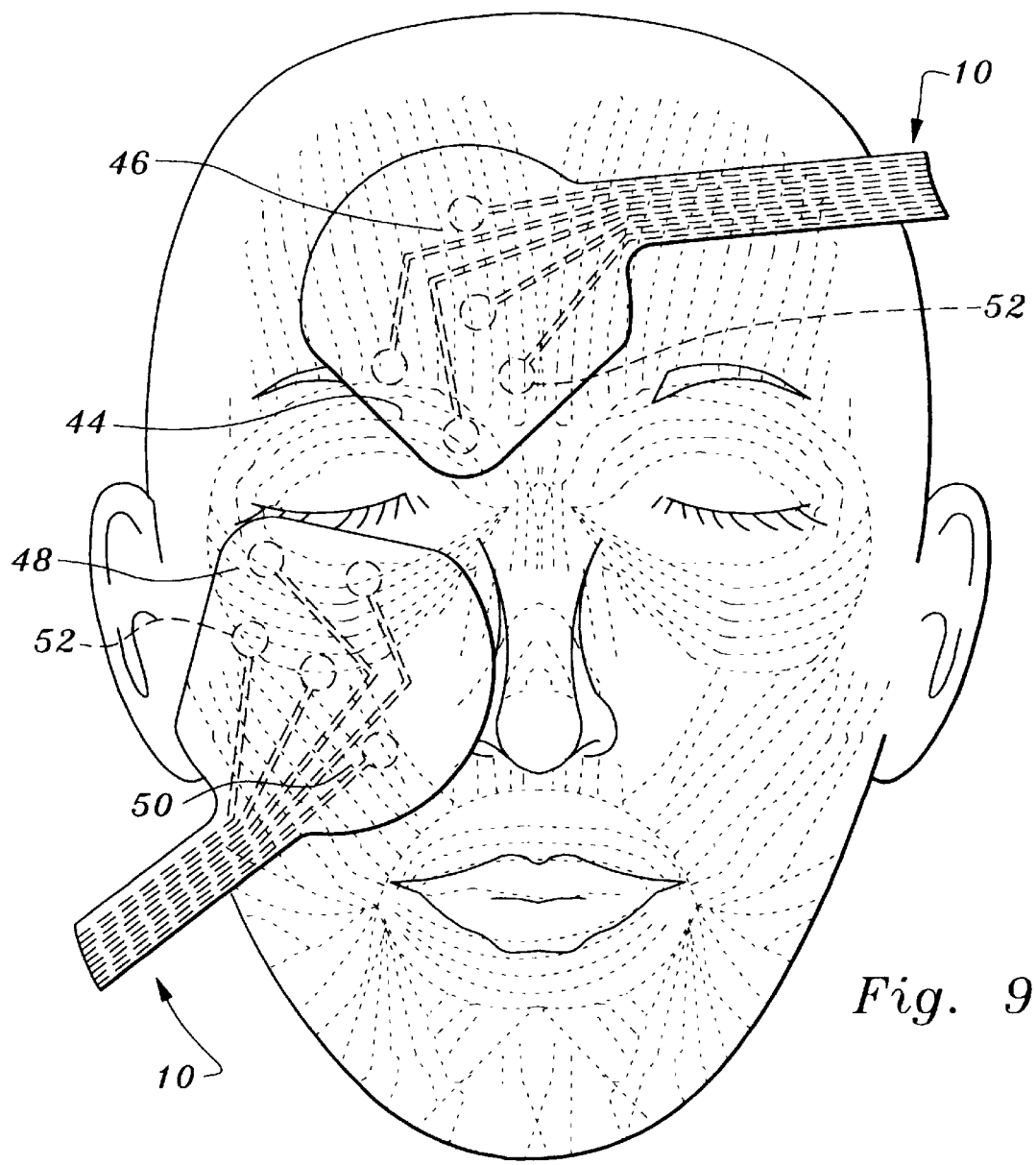
FIG. 9 is a front plan view of two two-muscle electrode assembly devices of this application in place on a person's face.

Now referring to FIG. 9, two-muscle electrode assemblies 10 have been applied to different areas of a human face. The uppermost assembly 10 is applied to the corrugator 44 facial muscle group and the frontalis 46 facial muscle group. For the lower electrode assembly, the orbicularis oculi 48 facial muscle group is contacted by the upper half of the electrode. The lower inner electrode contact points are over the zygomatic facial muscle group 50. Ground electrodes 52 are also present in each electrode assembly 10 shown in FIG. 3.

After applying the electrode assembly 10 with the electrolytic medium 40 in the electrode contact point wells, the heat of the patient's skin causes some mediums, such as the aforementioned Signa creme to partially liquefy and flow into the patient's sweat glands. This flow establishes better electrical contact and hence the electrode assembly 10 can better pick up the nerve impulses to the target muscle groups. If the electrotytic medium 40 does not liquefy, sometimes the patient's sweat glands produce perspiration which establishes a better electrical pick-up of nerve signals.

Figure 10:
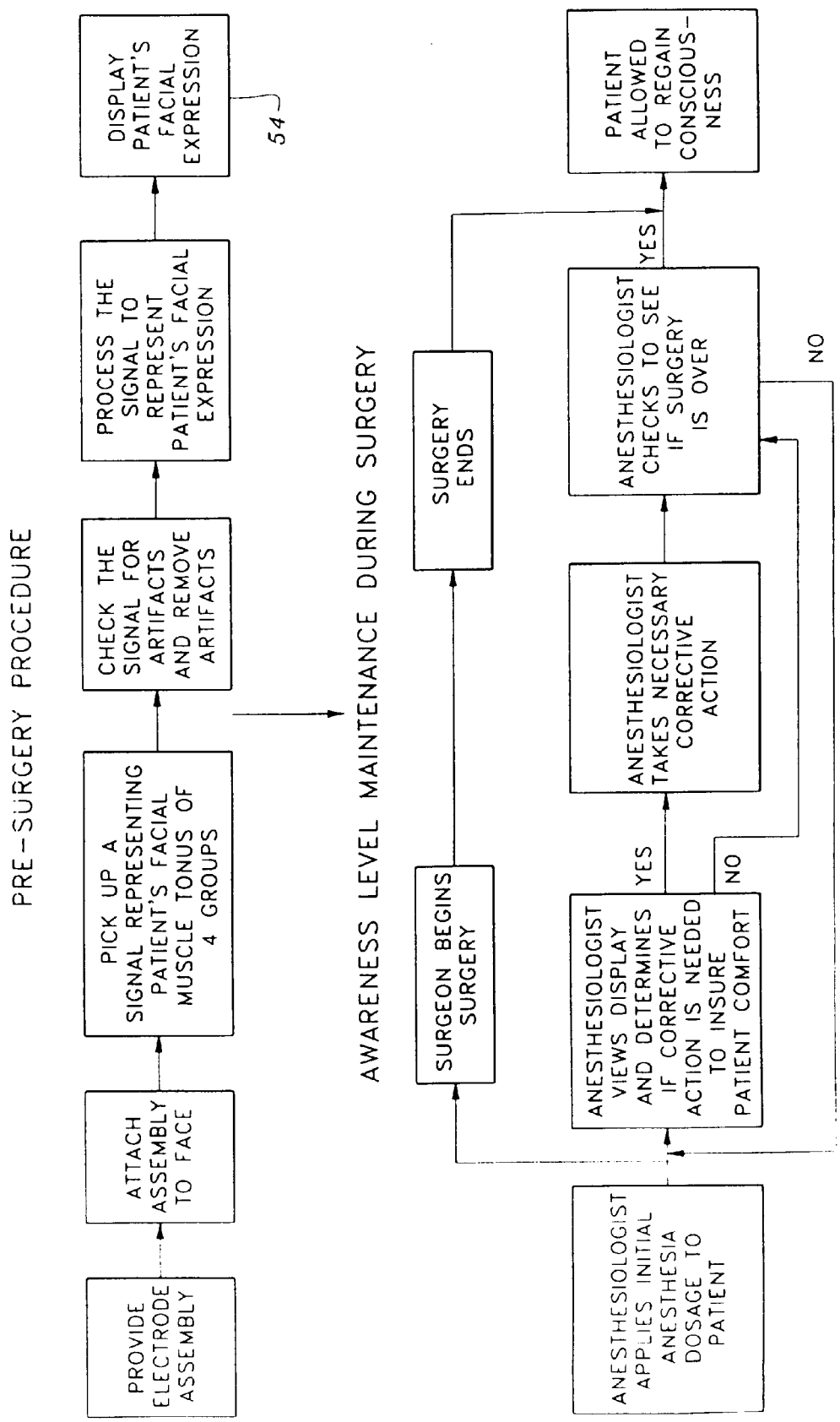
FIG. 10 is a block diagram representing the relationships of the steps of method of this application for sensing four facial muscle areas without active stimulation by the electrode assembly.

Referring now to FIG. 10, in use and operation the awareness level monitor receives signals from electrode assembly 10 placed upon the face of the patient. The monitor may be used by an anesthesiologist or other qualified operator to maintain the appropriate level of patient awareness during surgery. Initially, the anesthesiologist confirms the electrode assembly proper placement on the face of the patient. Base line reading may be then established. The patient is then given anesthesia appropriate for the circumstances. The anesthesiologist may then monitor the display 54 to determine the patient's level of awareness as reflected in changes in the muscle tonus. Once surgery begins, the anesthesiologist may use the display 54 to monitor the magnitude of the patient's response to what otherwise would be an objectively painful surgical stimulus. If the display 54 demonstrates an unacceptably high level of awareness and/or registration of pain, the anesthesiologist may administer more anesthesia or take other corrective action. If the display 54 demonstrates an unacceptably low level of awareness, other corrective measures may be taken. In this way the patient's comfort may be maximized and the patient's reaction to the surgical procedure and therefore recovery time can be minimized.

Also necessary to have a accurate display 54 is the removal of artifacts in the signal caused by such artifact generators as electric cauterizing devices. When this device is used, some electric current flows through the patient causing an anomaly in the signals as read by the electrode contact points 12. The artifact detector connected on one end to the cauterizing device or other artifact generator and on the other end to a first signal conduit. When an artifact is detected by the artifact detector, the detector then filters out the portion of the first signal representing the artifact.

Figure 11:
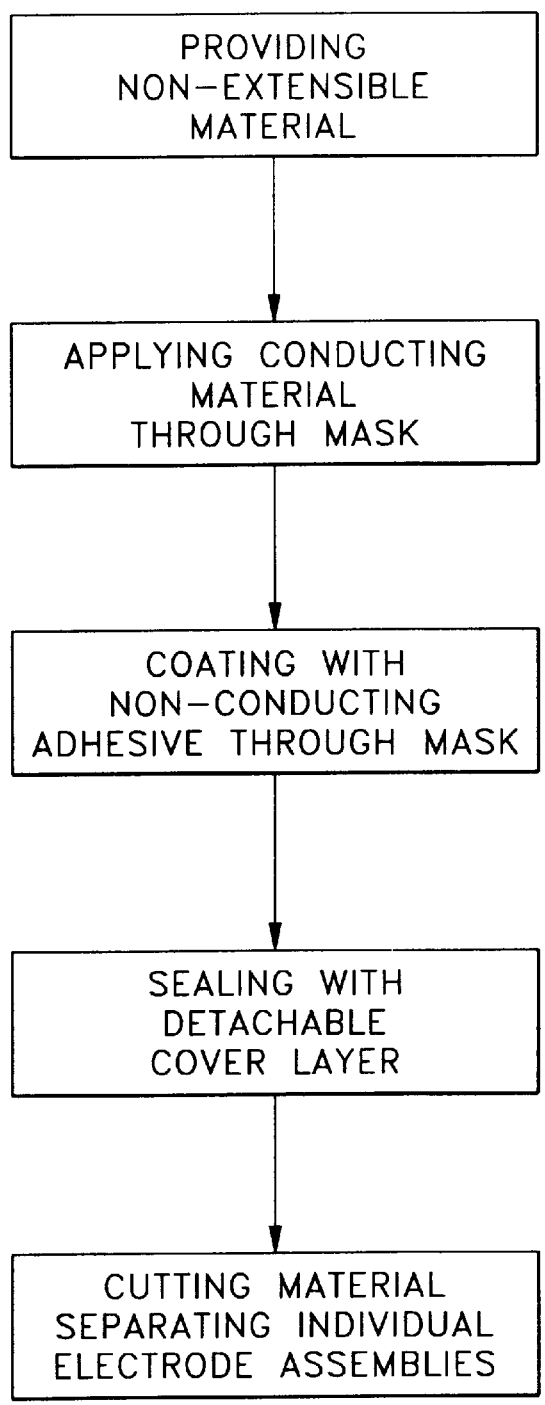
FIG. 11 is a block diagram representing the fabrication steps involved in manufacturing the electrode assembly devices of this application.

Referring now to FIG. 11, a block diagram showing the manufacturing method for providing an electrode assembly is displayed. The first step, as previously shown in FIGS. 3, 4, 5, and 6, is to provide a non-extensible material to serve as flexible layer 24. The next step is to apply electrically conductive material 16 through mask means 22 to flexible layer 24. After this is accomplished, the next step is to coat with a non-conducting adhesive 32, preferably through a mask means. As has been previously discussed this is one method. Other methods may include mating a pre-formed layer with the flexible layer 24 with attached pattern of electrically connecting paths 14. The next step is for a detachable pad 42 to be engaged with the now non-conducting adhesive coated flexible layer. Finally, if there are more than one electrode assemblies 10 on the flexible layer 24, the material must be cut so that the individual assemblies 10 can be separated.

Figure 12:
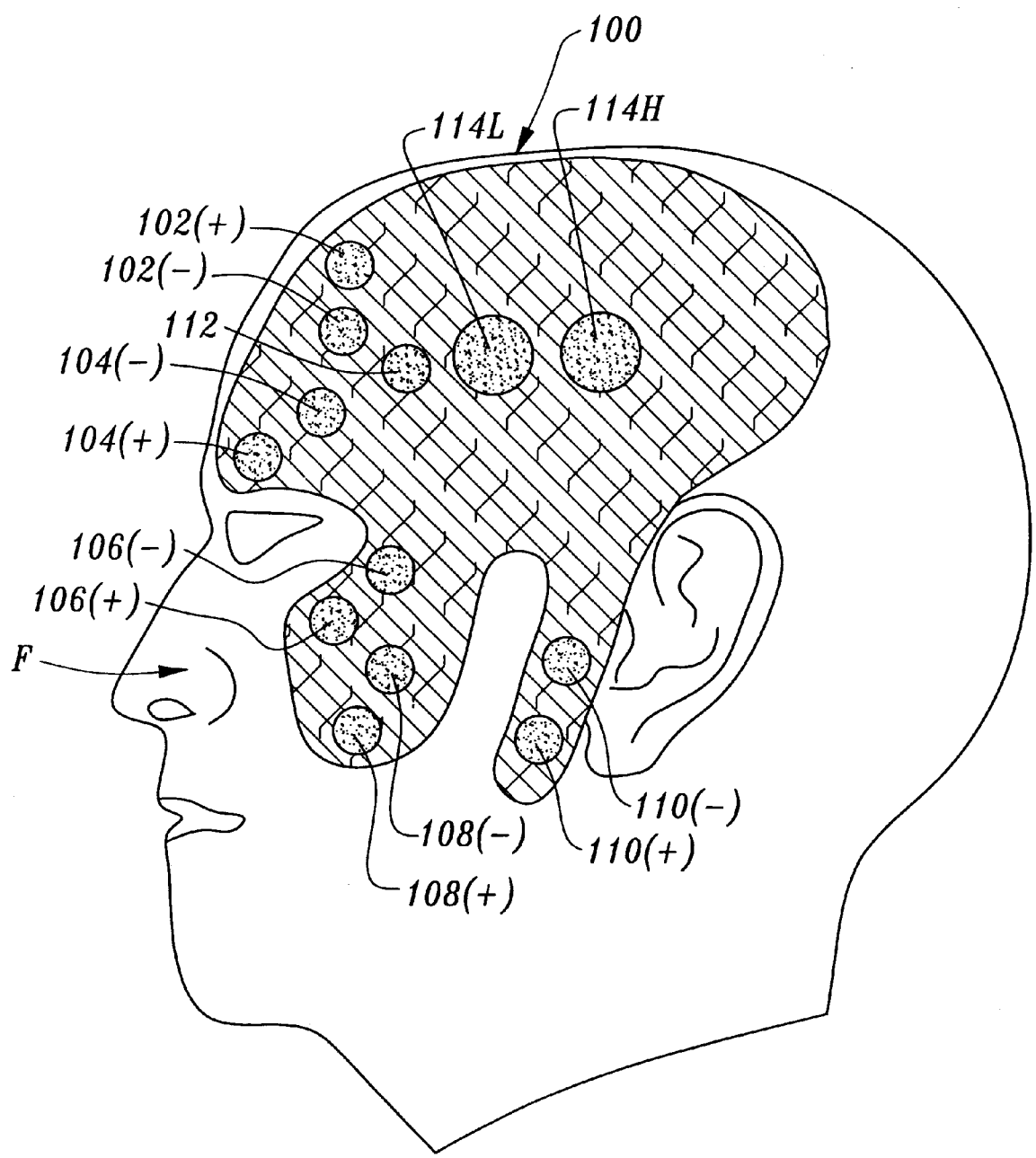
FIG. 12 is a partial perspective view of an alternative unitary electrode assembly, applied to the person's face, having electrode's for simultaneously sensing motion of five facial muscle areas as "Train of Four" and tetanic constant current nerve stimulation. However, this device may stimulate the nerve by interferential stimulation (i.e., applying two higher frequencies in order to obtain a low differential frequency for stimulation of the nerve).

Referring now to FIG. 12, an alternative electrode assembly or sensor-stimulator array 100 is shown as applied to a patient's face F to sense five muscle groups and stimulate at least one of the them according to the alternative method of this specification. This unitary and integrated sensor-stimulator array 100 is manufactured generally using the same techniques described above for the alternative two-muscle electrode assembly 10. The sensor-stimulator array 100 is, however, easier to apply and maintain in place on the face F of the patient than is the combination of two two-muscle electrode assemblies described in the First Bennett Patent.

The array 100 has a first sensor 102, a second sensor 104, a third sensor 106, a fourth sensor 108, a fifth sensor 110, a ground sensor 112, and a stimulator electrode 114. The first, second, third, fourth, and fifth sensors 102, 104, 106, 108, and 110 are mounted over the Frontalis, Corrugator, Orbicularis Oculi, Zygomatic, and Masseter muscle groups, respectively. The first through fifth sensors 102, 104, 106, 108, 110 each have two electrodes or electrode sensors, each such pairing being denoted as + or − in the numbering for the particular electrode pair (e.g., 102+ and 102− as the pair for the first or Frontalis sensor 102).

Figure 15:
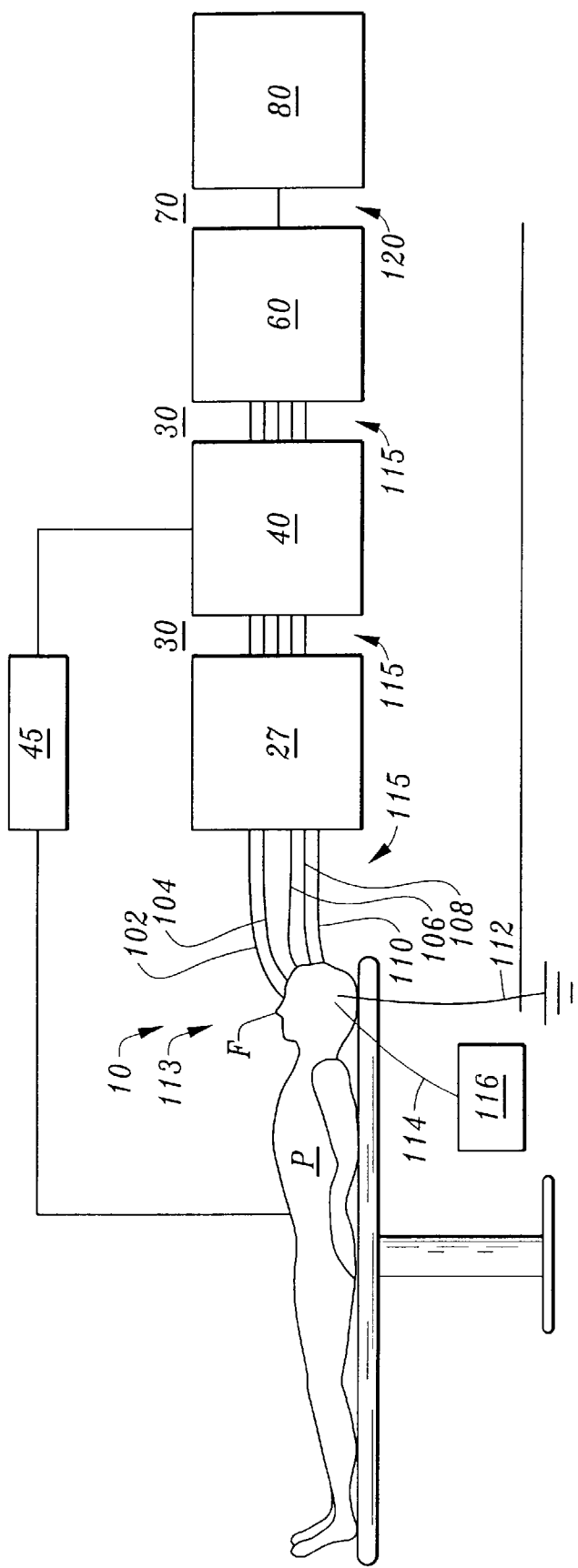
FIG. 15 is a block diagram representing the general relationships of the elements of the alternative device and method of this application for sensing five muscle areas and stimulating one muscle area.

The first through fifth sensors 102, 104, 106, 108, 110 and ground sensor 112 are generally constructed as described the First Bennett Patent. As a result, each sensor 102, 104, 106, 108, 110 and ground sensor 112 collectively generate, as shown in FIG. 15, the collective five-muscle signal or group of signals 115 of this alternative monitoring device, generally 113, and method. The five-muscle signal 115 is then passed through a pre-amplifier 27 and processed in generally the same fashion as described in the First Bennett Patent with the modifications and additions described herein. Referring back to FIG. 12, the stimulator sensor 114 of this alternative embodiment 100 utilizes stimulator electrodes or electrode sensors 114H and 114L to stimulate the upper branch of the facial nerve for recording at the Corrugator muscle in the patient's face F. (Alternatively, the stimulator sensor 114 could instead consist of a muscle sensor such as one of the first through fifth muscle sensors 102, 104, 106, 108, 110.) By this device and method, the facial muscle nerve lying under the surface of the skin can be activated without trauma to the nerve or tissues of the patient. The stimulator sensor 114H, 114L is connected to, as shown in FIG. 15, a stimulator activation device 116 of the type well known in the art. Upon temporary suspension of recording of electromyograms by the monitoring device 113, the stimulator activation device 116 can be activated by an operator or anesthetist (not shown) to preferably carry to the patient's face F through the stimulator sensor 114 four equally spaced electrical pulses 50 microseconds in duration each presented as a square wave at a frequency of 2 Hz. Optionally, and referring to FIG. 12, the pulses on the first stimulator electrode 114H have a carrier frequency of 10,050 Hz, and the pulses on the second stimulator electrode 116L have a carrier frequency of 10,000 Hz. In this embodiment, one of the two sensors serves as the electrical return for the current. The two high difference frequencies delivered by stimulator sensors 114H, 114L stimulate the Corrugator nerve at the much lower interferential frequency generated between them, 50 Hz. The high difference frequencies of the stimulator sensors 114H, 114L penetrate biological tissues more effectively than lower frequencies but are not effective at stimulating muscles within the tissues. The resulting interferential low-frequency 10 Hz pulses delivered to the Corrugator nerve are highly effective at stimulating nerves such as the Corrugator nerve deep under the skin of the patient's face F.

Immediately after such stimulation, the second sensor 104 records a stimulation signal based on the level of resulting activity in the Corrugator muscle area in the face F. As shown in FIG. 15, this stimulation signal is transmitted to the computer 60, which records the signal, processes it according the algorithms loaded in the computer 60, and generates a display of the level of activity on the display 80.

Figure 16:
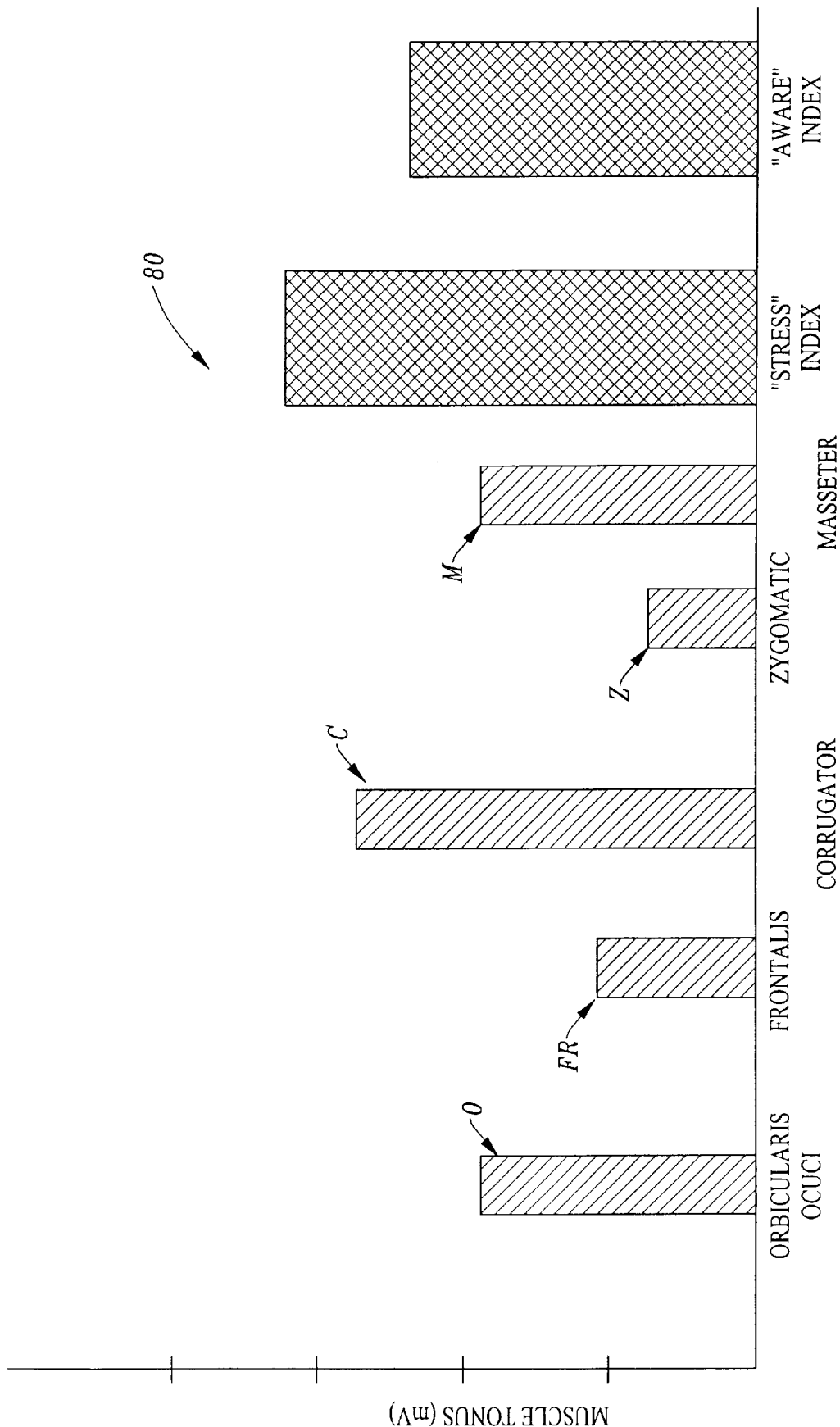
FIG. 16 is a plan view of one possible output for display in the alternative device of this application for sensing five muscle areas and stimulating one muscle area.

Upon resumption of the recording of electromyograms by the monitoring device 113, the five-muscle activity signal 115 is again transmitted to pre-amplifier 27, through the detector 40, and into the computer 60. The computer applies an "Aware" and a "Stress" algorithm to the signal 115 and creates a second signal 120. This second signal or group of signals 120 represents, and causes the display 80 to show: (1) the facial expression of the patient P such as described in the First Bennett Patent; and/or (2) as shown in FIG. 16, a graphical representation of the activity sensed for each of the five facial muscle areas and a "Stress" and "Aware" index.

The "Aware" algorithm for determining the "Aware Index" is a summation index using the following formula:

$$O+F+C+Z=\text{"Aware Index"}$$

Where:
O is the muscle tonus of Orbicularis Oculi muscle,
F is the muscle tonus of the Frontalis muscle,
C is the muscle tonus of the Corrugator muscle,
Z is the muscle tonus of the Zygomatic muscle, and
The "Stress" algorithm for determining the "Stress Index" is a differential or ratio based index, preferably using the following formula with the same nomenclature as set forth above:

Stress Algorithm a) IF $[O \geq Z]$ or $[O < Z$ and $C \leq F]$, then
$$\text{Stress} = \left(\frac{(C-F)+(O-Z)}{C+F+O+Z}\right) \times 100$$

b) IF $[O < Z]$ and $[C > F]$, then
$$\text{Stress} = \left(\frac{(C-F)+(M-Z)}{C+F+M+Z}\right) \times 100$$

c) $M$ is displayed separately in all cases as $M$

The Aware algorithm and resulting index provides a measure of the degree of patient oblivion and unconsciousness. However, because this algorithm is a summation of muscle tonus values which will diminish due to muscle paralysis brought about by anesthesia, the Aware Index should be calibrated to adjust for the level of paralysis of the facial muscles. This is accomplished by having determined an original unparalyzed Corrugator stimulator signal, as described above, prior to administration of anesthesia. Upon administration of anesthesia, a subsequent Corrugator stimulator signal is determined, again according to the method described above. The degree of paralysis of the facial muscles is measured by the percentage change of the stimulator signal from the unparalyzed to the anesthetized state. Since muscle activity is inversely proportional to the degree of paralysis, the computer 60 multiplies the Aware value calculated during stimulation under anesthesia, at that particular point in time, by the inverse of the remaining level of activity as compared to the original, unparalyzed state, except in the event of total paralysis when the remaining activity level is null. Thus, if the Aware value calculated by stimulation during anesthesia is 5% as great as that calculated before applying anesthesia, the computer 60 multiplies the Aware value during anesthesia at that point in time by a factor of 20 and displays the resulting Aware Index on the display 80. In the event that the remaining activity level is null, the computer 60 generates an Aware Index of zero.

This method of stimulation and comparison of muscle activity from the pre-anesthesia to the anesthetized state thus provides a monitor for more precise titration of anesthetic agents during administration of anesthesia. In addition, in the event of total paralysis or neuro muscular block of the facial muscles, the Aware Index will be zero and the resulting display of a zero value for the Aware Index on the display 80. The anesthesiologist is thus alerted to the state of total paralysis of the facial muscles as well as the inability to rely on any measurement of muscle activity in the face to indicate the patient's true level of consciousness in view of the total paralysis of the facial muscles.

Except in the case of total paralysis indicated by the zeroing of the Aware Index, the Stress algorithm provides a signal based on the output from the lower brain centers of the basal ganglia and limbic systems directly to the patterning of facial muscles. These signals, known as facial expressions, are the result of the combination of patient arousal, pharmacological and anesthetic drug states, and surgical stimulation. By providing a Stress Index based on these signals, the anesthesiologist is provided with an indicator of the true state of analgesia and a significant tool for more precise titration of analgesic agents.

Figure 13:
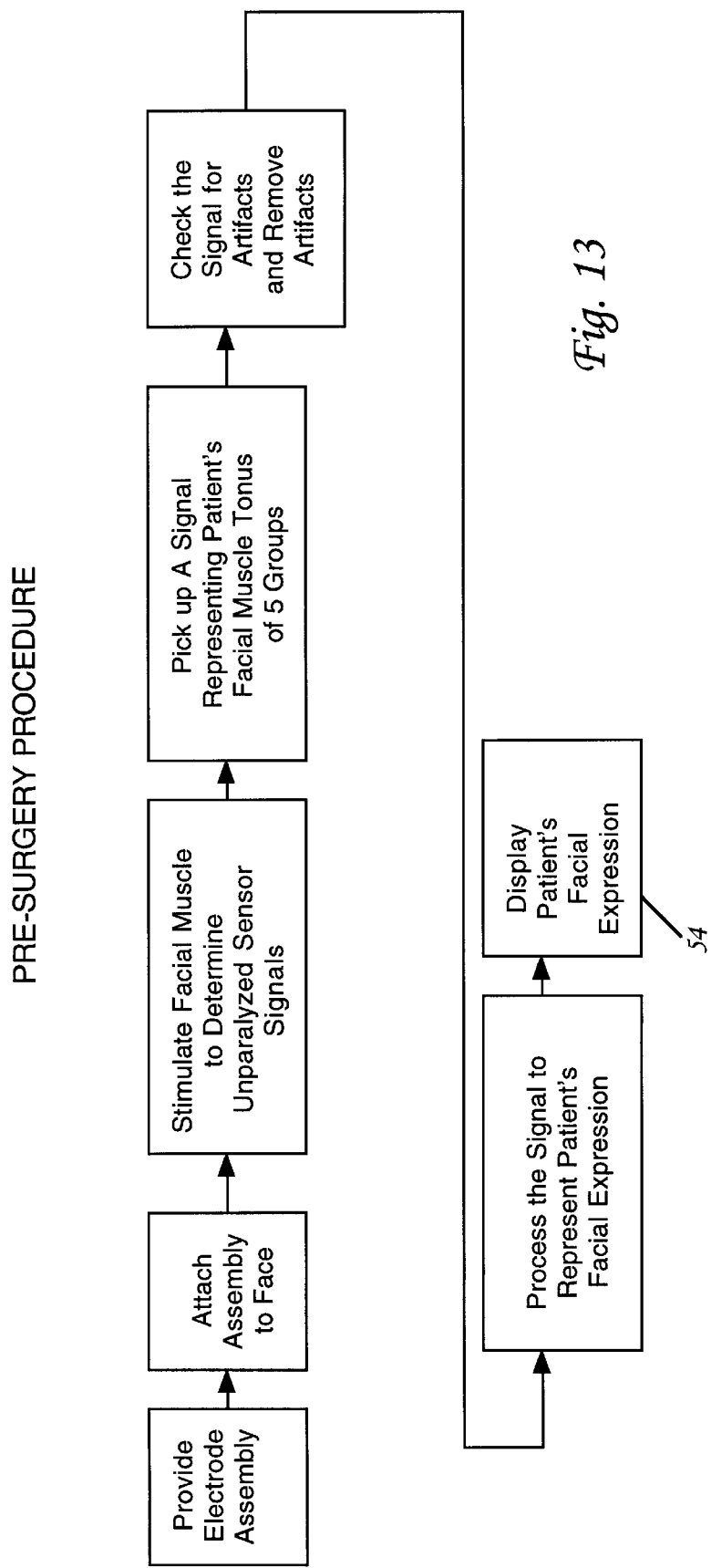
FIG. 13 is a block diagram representing the relationships of the pre-surgery steps of the alternative method of this specification for sensing five facial muscle areas and actively stimulating a muscle area with the five-muscle electrode assembly.
Figure 14:
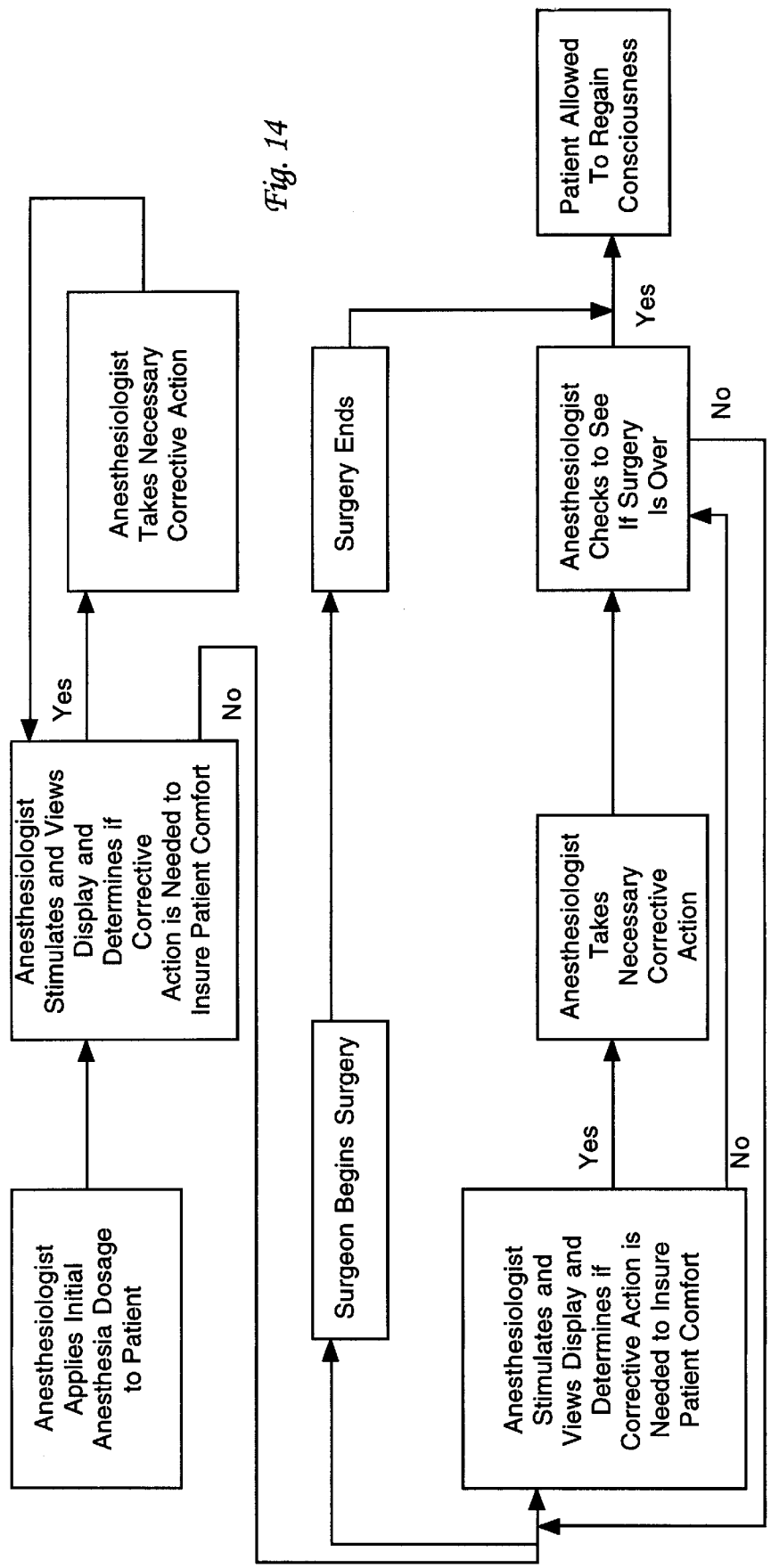
FIG. 14 is a block diagram representing the relationships of the steps of the alternative method of this specification for sensing five facial muscle areas and actively stimulating a muscle area with the five-muscle electrode assembly during surgery.

In use and operation, the consciousness or anesthesia adequacy monitor 10 may be used by an anesthesiologist or other operator to monitor and/or maintain patient consciousness as desired during administration of anesthesia as suggested in FIGS. 13 and 14. Initially, the anesthesiologist configures the sensor array (100 in FIG. 12) on the face F of the patient P. Referring now to FIG. 14, the patient P is the given anesthesia appropriate for the circumstances. As shown in FIG. 13, a base line reading may then be established, including stimulation of the facial muscle to determine the response level of the facial muscles in the completely unparalyzed state. The anesthesiologist may then monitor the display 80, and as desired stimulate the patient's facial nerve, to determine the patient's level of paralysis and consciousness as reflected by changes in muscle tonus reported on the display 80. The device preferably includes an automatic mode to stimulate at regular intervals. Initial calibration in the anesthetized, but unparalyzed state, then rapid repetitions for 5 minutes every 15 seconds, then once ever 4–5 seconds thereafter using the "train of four" method previously described. Once the surgery begins, the anesthesiologist may use the display 80 to monitor the magnitude of the patient's response to surgery, including my intermittent stimulation of the patient's facial nerve. If the display demonstrates an unacceptably high level of patient awareness, or total paralysis of the facial muscles, the anesthesiologist may take corrective action. In this way, the patient's comfort can be maximized and the patient's reaction to surgery, and therefore the patient's recovery time, can be minimized.

As also noted in the First Bennett Patent, the consciousness monitoring device 10 may also be used with a patient who has suffered injury and is experiencing a diminished level of consciousness. The device 10, or portions thereof, may also be used in other settings in which consciousness monitoring is desired. The device may be used as well in ICU for titrating sedation, analgesia and/or paralysis.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. An apparatus for indicating the consciousness of a person, comprising in combination:

(A) an array of facial muscle sensors adapted to generate sensor signals representing the simultaneous activity of at least four different facial muscle areas, each of which elicit distinctive patterns of facial expressions of the person;

(B) a sensor signal processor operatively coupled to the sensors to receive the sensor signals from the facial muscle sensors and, based on the sensor signals, automatically generate an output signal indicating the consciousness of the person;

wherein the facial muscle sensors are surface electromyograms adapted to be physically attached the person's face in positions allowing the monitoring of the different facial muscles: and also having: (i) a facial muscle stimulator adapted to activate a facial nerve in at least one of said facial muscle areas, and (ii) a facial nerve processor adapted to (a) receive sensor signals from the facial muscles sensors in said nerve-activated facial muscle area, (b) determine a paralysis level for said nerve-activated facial muscle area, and (c) adjust the sensor signal processor's generation of at least a portion of the output signal according to the determined paralysis level, whereby the output signal indicates the consciousness of the person despite partial paralysis of the nerve-activated facial muscle area.

2. The consciousness indicating apparatus of claim 1 wherein said facial muscle areas are selected from among the frontalis area, the corrugator area, the zygomatic area, the masseter area, and the orbilaris oculi area.

3. The consciousness indicating apparatus of claim 1 wherein the facial muscle stimulator includes a first facial muscle stimulator providing a first carrier signal at a first predetermined frequency to one facial muscle area and a second facial muscle stimulator providing a second carrier signal at a second predetermined frequency to the one facial muscle area, whereby the first and second facial muscle stimulators cooperatively stimulate a facial nerve in the one facial muscle area at a third stimulation frequency comprising the difference between the first and second predetermined frequencies.

4. The consciousness indicating apparatus of claim 3 wherein said facial muscle areas are selected from among the frontalis area, the corrugator area, the zygomatic area, the masseter area, and the orbilaris oculi area.

5. The consciousness indicating apparatus claim 4 also having an artifact filter for filtering the sensor signals received by the sensor signal processor to remove an artifact representing muscle activity caused by known stimulus to the person not indicative of the person's consciousness, whereby the output signal generated by the sensor signal processor indicates the consciousness of the person without unwanted distortion from such artifact.

6. The consciousness indicating apparatus of claim 5 wherein the artifact filter includes an artifact detector connected to an external device to provide a detection signal to the artifact filter upon activation of the external device.

7. The consciousness indicating apparatus of claim 1 also including a display operatively connected to the sensor signal processor to display a consciousness level for the person indicated by the output signal generated by the signal processor.

8. The consciousness indicating apparatus of claim 2 also including a display operatively connected to the sensor signal processor to display a consciousness level for the person indicated by the output signal generated by the signal processor.

9. The consciousness indicating apparatus of claim 3 also including a display operatively connected to the sensor signal processor to display a consciousness level for the person indicated by the output signal generated by the signal processor.

10. The consciousness indicating apparatus of claim 4 also including a single computing device to perform the computing for the sensor computing processor and the facial nerve processor.

11. The apparatus of claim 1 in which the array of facial muscle sensors is also adapted to generate sensor signals representing the simultaneous activity of a fifth different facial muscle area.

12. The apparatus of claim 3 in which the array of facial muscle sensors is also adapted to generate sensor signals representing the simultaneous activity of a fifth different facial muscle area.

13. The apparatus of claim 4 in which the array of facial muscle sensors is also adapted to generate sensor signals representing the simultaneous activity of a fifth different facial muscle area.

14. The apparatus of claim 6 in which the array of facial muscle sensors is also adapted to generate sensor signals representing the simultaneous activity of a fifth different facial muscle area.

15. The consciousness indicating apparatus of claim 1 wherein the sensor signal processor generates at least a portion of the output signal based on relative differences among the sensor signals and thereby the different activities of the different facial muscle areas represented by the sensor signals.

16. The consciousness indicating apparatus of claim 15 wherein the sensor signal processor also generates at least a summed portion of the output signal based on the summation of the sensor signals and thereby the different activities of the different facial muscle areas represented by the sensor signals.

17. The consciousness indicating apparatus of claim 3 wherein the sensor signal processor generates at least a portion of the output signal based on relative differences among the sensor signals and thereby the different activities of the different facial muscle areas represented by the sensor signals.

18. The consciousness indicating apparatus of claim 17 wherein the sensor signal processor also generates at least a summed portion of the output signal based on the summation of the sensor signals and thereby the different activities of the different facial muscle areas represented by the sensor signals.

19. The consciousness indicating apparatus of claim 4 wherein the sensor signal processor generates at least a portion of the output signal based on relative differences among the sensor signals and thereby the different activities of the different facial muscle areas represented by the sensor signals.

20. The consciousness indicating apparatus of claim 19 wherein the sensor signal processor also generates at least a summed portion of the output signal based on the summation of the sensor signals and thereby the different activities of the different facial muscle areas represented by the sensor signals.

21. The consciousness indicating apparatus of claim 5 wherein the sensor signal processor generates at least a portion of the output signal based on relative differences among the sensor signals and thereby the different activities of the different facial muscle areas represented by the sensor signals.

22. The consciousness indicating apparatus of claim 21 wherein the sensor signal processor also generates at least a summed portion of the output signal based on the summation of the sensor signals and thereby the different activities of the different facial muscle areas represented by the sensor signals.

23. The consciousness indicating apparatus of claim 6 wherein the sensor signal processor generates at least a portion of the output signal based on relative differences among the sensor signals and thereby the different activities of the different facial muscle areas represented by the sensor signals.

24. The consciousness indicating apparatus of claim 23 wherein the sensor signal processor also generates at least a summed portion of the output signal based on the summation of the sensor signals and thereby the different activities of the different facial muscle areas represented by the sensor signals.

25. The consciousness indicating apparatus of claim 1 wherein the sensor signal processor generates at least a portion of the output signal based on relative differences among the sensor signals and thereby the different activities of the different facial muscle areas represented by the sensor signals.

26. The consciousness indicating apparatus of claim 25 wherein the sensor signal processor also generates at least a summed portion of the output signal based on the summation of the sensor signals and thereby the different activities of the different facial muscle areas represented by the sensor signals.

27. An apparatus for indicating the consciousness of a person, comprising in combination:
   an array of facial muscle sensors adapted to generate sensor signals representing the simultaneous activity of at least four different facial muscle areas, each of which elicit distinctive patterns of facial expressions of the person;
   a sensor signal processor operatively coupled to the sensors to receive the sensor signals from the facial muscle sensors and, based on the sensor signals, automatically generate an output signal indicating the consciousness of the person;
   wherein the facial muscle sensors are surface electromyograms adapted to be physically attached to the person's face in positions allowing the monitoring of the different facial muscles;
   wherein said facial muscle areas are selected from among the frontalis area, the corrugator area, the zygomatic area, the masseter area, and the orbilaris oculi area; and
   in which the array of facial muscle sensors is also adapted to generate sensor signals representing the simultaneous activity of a fifth different facial muscle area.

28. The consciousness indicating apparatus of claim 27 wherein the sensor signal processor generates at least a portion of the output signal based on relative differences among the sensor signals and thereby the different activities of the different facial muscle areas represented by the sensor signals.

29. The consciousness indicating apparatus of claim 28 wherein the sensor signal processor also generates at least a summed portion of the output signal based on the summation of the sensor signals and thereby the different activities of the different facial muscle areas represented by the sensor signals.

30. An apparatus for indicating the consciousness of a person, comprising in combination:
   an array of facial muscle sensors adapted to generate sensor signals representing the simultaneous activity of at least four different facial muscle areas, each of which elicit distinctive patterns of facial expressions of the person;
   a sensor signal processor operatively coupled to the sensors to receive the sensor signals from the facial muscle sensors and, based on the sensor signals, automatically generate an output signal indicating the consciousness of the person;

also including a display operatively connected to the sensor signal processor to display a consciousness level for the person indicated by the output signal generated by the signal processor; and in which the array of facial muscle sensors is also adapted to generate sensor signals representing the simultaneous activity of a fifth different facial muscle area.

31. An apparatus for indicating the consciousness of a person, comprising in combination:

at least one facial muscle sensor grouping adapted to generate a first sensor signal representing the activity of a first facial muscle area that elicits a first portion of the facial expression of the person:

a facial muscle stimulator adapted to activate a facial nerve in said first facial muscle area;

a processor apparatus operatively coupled to the at least one facial muscle sensor grouping to (i) receive at least the first sensor signal from a first facial muscle sensor grouping, (ii) determine a paralysis level for the facial muscle area based on the first sensor signal received subsequent to activation of the facial nerve by the facial muscle stimulator, and (iii) generate an output signal based on at least the first sensor signal and the determined paralysis level, whereby the output signal indicates the consciousness of the person despite partial paralysis of the nerve-activated first facial muscle area; and wherein the facial muscle stimulator includes a first facial muscle stimulator providing a first carrier signal at a first predetermined frequency to the facial muscle area, and a second facial muscle stimulator providing a second carrier signal at a second predetermined frequency to the first facial muscle area, whereby the first and second facial muscle stimulators cooperatively stimulate a facial nerve in the first facial muscle area at a third stimulation frequency comprising the difference between the first and second predetermined frequencies.

32. The consciousness indicating apparatus of claim 31 wherein the first and second facial stimulators each also comprise a facial muscle sensor.

33. The consciousness indicating apparatus of claims 32 includes (i) at least a second facial muscle sensor grouping including the second facial muscle stimulator, said second grouping being adapted to generate a second sensor signal representing the activity of a second facial muscle area that elicits a second portion of the facial expression of the person, and (ii) the processor apparatus is operatively connected to the second facial muscle sensor grouping to also receive the second sensor signal and utilize the second sensor signal to generate the output signal.

34. The consciousness indicating apparatus of claim 33 wherein each facial muscle sensor grouping includes a surface electromyogram adapted to be physically attached the person's on face in position allowing the monitoring of a facial muscle.

35. The consciousness indicating apparatus claim 34 also having an artifact filter for filtering the sensor signals received by the processor apparatus to remove an artifact representing muscle activity caused by known stimulus to the person not indicative of the person's consciousness, whereby the output signal generated by the processor indicates the consciousness of the person with reduced distortion from such artifact.

36. The consciousness indicating apparatus of claim 35 wherein the artifact filter includes an artifact detector connected to an external device adapted to interact with the person, said detector providing a detection signal to the artifact filter upon activation of the external device to interact with the person.

37. The consciousness indicating apparatus of claim 31 also including a display operatively connected to the sensor signal processor to display a consciousness level for the person indicated by the output signal generated by the signal processor.

38. The consciousness indicating apparatus of claim 33 also including a display operatively connected to the sensor signal processor to display a consciousness level for the person indicated by the output signal generated by the signal processor.

39. The consciousness indicating apparatus of claim 34 also including a display operatively connected to the sensor signal processor to display a consciousness level for the person indicated by the output signal generated by the signal processor.

40. The consciousness indicating apparatus of claim 35 also including a display operatively connected to the sensor signal processor to display a consciousness level for the person indicated by the output signal generated by the signal processor.

41. The consciousness indicating apparatus of claim 36 also including a display operatively connected to the sensor signal processor to display a consciousness level for the person indicated by the output signal generated by the signal processor.

42. The consciousness indicating apparatus of claim 31 also including second, third, fourth, and fifth facial muscle sensor groupings adapted to respectively generate second, third, forth, and fifth sensor signals from distinct facial muscle areas on the person, and wherein the processor apparatus is operatively coupled to each such facial muscle sensor grouping to also receive, and to generate the output signal also on, the second, third, fourth, and fifth sensor signals.

43. The consciousness indicating apparatus of claim 32 also including second, third, fourth, and fifth facial muscle sensor groupings adapted to respectively generate second, third, forth, and fifth sensor signals from distinct facial muscle areas on the person, and wherein the processor apparatus is operatively coupled to each such facial muscle sensor grouping to also receive, and to base the output signal also on, the second, third, fourth, and fifth sensor signals.

44. The consciousness indicating apparatus of claim 33 also including third, fourth, and fifth facial muscle sensor groupings adapted to respectively generate third, forth, and fifth sensor signals from distinct facial muscle areas on the person, and wherein the processor apparatus is operatively coupled to each such facial muscle sensor grouping to also receive, and to generate the output signal based also on, the third, fourth, and fifth sensor signals.

45. The consciousness indicating apparatus of claim 34 also including third, fourth, and fifth facial muscle sensor groupings adapted to respectively generate third, forth, and fifth sensor signals from distinct facial muscle areas on the person, and wherein the processor apparatus is operatively coupled to each such facial muscle sensor grouping to also receive, and to generate the output signal based also on, the third, fourth, and fifth sensor signals.

46. The consciousness indicating apparatus of claim 35 also including third, fourth, and fifth facial muscle sensor groupings adapted to respectively generate third, forth, and fifth sensor signals from distinct facial muscle areas on the person, and wherein the processor apparatus is operatively coupled to each such facial muscle sensor grouping to also receive, and to generate the output signal based also on, the third, fourth, and fifth sensor signals.

47. The consciousness indicating apparatus of claim 36 also including third, fourth, and fifth facial muscle sensor groupings adapted to respectively generate third, forth, and fifth sensor signals from distinct facial muscle areas on the person, and wherein the processor apparatus is operatively coupled to each such facial muscle sensor grouping to also receive, and to generate the output signal based also on, the third, fourth, and fifth sensor signals.

48. The consciousness indicating apparatus of claim 41 also including third, fourth, and fifth facial muscle sensor groupings adapted to respectively generate third, forth, and fifth sensor signals from distinct facial muscle areas on the person, and wherein the processor apparatus is operatively coupled to each such facial muscle sensor grouping to also receive, and to generate the output signal based also on, the third, fourth, and fifth sensor signals.

49. The consciousness indicating apparatus of claim 33 wherein the sensor signal processor generates at least a portion of the output signal based on relative differences among the sensor signals and thereby the different activities of the different facial muscle areas represented by the sensor signals.

50. The consciousness indicating apparatus of claim 49 wherein the sensor signal processor also generates at least a summed portion of the output signal based on the summation of the sensor signals and thereby the different activities of the different facial muscle areas represented by the sensor signals.

51. The consciousness indicating apparatus of claim 34 wherein the sensor signal processor generates at least a portion of the output signal based on relative differences among the sensor signals and thereby the different activities of the different facial muscle areas represented by the sensor signals.

52. The consciousness indicating apparatus of claim 51 wherein the sensor signal processor also generates at least a summed portion of the output signal based on the summation of the sensor signals and thereby the different activities of the different facial muscle areas represented by the sensor signals.

53. The consciousness indicating apparatus of claim 39 wherein the sensor signal processor generates at least a portion of the output signal based on relative differences among the sensor signals and thereby the different activities of the different facial muscle areas represented by the sensor signals.

54. The consciousness indicating apparatus of claim 53 wherein the sensor signal processor also generates at least a summed portion of the output signal based on the summation of the sensor signals and thereby the different activities of the different facial muscle areas represented by the sensor signals.

55. The consciousness indicating apparatus of claim 42 wherein the sensor signal processor generates at least a portion of the output signal based on relative differences among the sensor signals and thereby the different activities of the different facial muscle areas represented by the sensor signals.

56. The consciousness indicating apparatus of claim 55 wherein the sensor signal processor also generates at least a summed portion of the output signal based on the summation of the sensor signals and thereby the different activities of the different facial muscle areas represented by the sensor signals.

57. The consciousness indicating apparatus of claim 43 wherein the sensor signal processor generates at least a portion of the output signal based on relative differences among the sensor signals and thereby the different activities of the different facial muscle areas represented by the sensor signals.

58. The consciousness indicating apparatus of claim 57 wherein the sensor signal processor also generates at least a summed portion of the output signal based on the summation of the sensor signals and thereby the different activities of the different facial muscle areas represented by the sensor signals.

59. The consciousness indicating apparatus of claim 45 wherein the sensor signal processor generates at least a portion of the output signal based on relative differences among the sensor signals and thereby the different activities of the different facial muscle areas represented by the sensor signals.

60. The consciousness indicating apparatus of claim 59 wherein the sensor signal processor also generates at least a summed portion of the output signal based on the summation of the sensor signals and thereby the different activities of the different facial muscle areas represented by the sensor signals.

61. The consciousness indicating apparatus of claim 35 wherein said facial muscle areas are selected from among the frontalis area, the corrugator area, the zygomatic area, the masseter area, and the orbicularis oculi area.

62. The consciousness indicating apparatus of claim 46 wherein said facial muscle areas are selected from among the frontalis area, the corrugator area, the zygomatic area, the masseter area, and the orbicularis oculi area.

63. The consciousness indicating apparatus of claim 53 wherein said facial muscle areas are selected from among the frontalis area, the corrugator area, the zygomatic area, the masseter area, and the orbicularis oculi area.

64. The consciousness indicating apparatus of claim 54 wherein said facial muscle areas are selected from among the frontalis area, the corrugator area, the zygomatic area, the masseter area, and the orbicularis oculi area.

65. An apparatus for indicating the consciousness of a person, comprising in combination:

at least one facial muscle sensor grouping adapted to generate a first sensor signal representing the activity of a first facial muscle area that elicits a first portion of the facial expression of the person;

a facial muscle stimulator adapted to activate a facial nerve in said first facial muscle area; a processor apparatus operatively coupled to the at least one facial muscle sensor grouping to (i) receive at least the first sensor signal from a first facial muscle sensor grouping, (ii) determine a paralysis level for the facial muscle area based on the first sensor signal received subsequent to activation of the facial nerve by the facial muscle stimulator, and (iii) generate an output signal based on at least the first sensor signal and the determined paralysis level, whereby the output signal indicates the consciousness of the person despite partial paralysis of the nerve-activated first facial muscle area; and also including second, third, fourth, and fifth facial muscle sensor groupings adapted to respectively generate second, third, forth, and fifth sensor signals from distinct facial muscle areas on the person, and wherein the processor apparatus is operatively coupled to each such facial muscle sensor grouping to also receive, and to generate the output signal based also on, the second, third, fourth, and fifth sensor signals.

66. The consciousness indicating apparatus of claim 65 wherein the sensor signal processor generates at least a portion of the output signal based on relative differences among the sensor signals and thereby the different activities of the different facial muscle areas represented by the sensor signals.

67. The consciousness indicating apparatus of claim 66 wherein the sensor signal processor also generates at least a summed portion of the output signal based on the summation of the sensor signals and thereby the different activities of the different facial muscle areas represented by the sensor signals.

68. The consciousness indicating apparatus of claim 65 wherein said facial muscle areas are selected from among the frontalis area, the corrugator area, the zygomatic area, the masseter area, and the orbicularis oculi area.

69. The consciousness indicating apparatus of claim 65
also including a display operatively connected to the sensor signal processor to display a consciousness level for the person indicated by the output signal generated by the signal processor.

70. The consciousness indicating apparatus of claim 69 wherein the sensor signal processor generates at least a portion of the output signal based on relative differences among the sensor signals and thereby the different activities of the different facial muscle areas represented by the sensor signals.

71. The consciousness indicating apparatus of claim 70 wherein the sensor signal processor also generates at least a summed portion of the output signal based on the summation of the sensor signals and thereby the different activities of the different facial muscle areas represented by the sensor signals.

72. An apparatus for indicating the consciousness of a person, comprising in combination:

(A) an array of facial muscle sensors adapted to generate sensor signals representing the simultaneous activity of at least four different facial muscle areas, each of which elicit distinctive patterns of facial expressions of the person;

(B) a sensor signal processor operatively coupled to the sensors to receive the sensor signals from the facial muscle sensors and, based on the sensor signals, automatically generate an output signal indicating the consciousness of the person;

wherein the facial muscle sensors are surface electromyograms adapted to be physically attached the person's face in positions allowing the monitoring of the different facial muscles; and wherein the sensor signal processor generates at least a patterned portion of the output signal based on relative differences among the sensor signals and thereby the different activities of the different facial muscle areas represented by the sensor signals.

73. The consciousness indicating apparatus of claim 72 wherein the sensor signal processor also generates at least a summed portion of the output signal based on the summation of the sensor signals and thereby the different activities of the different facial muscle areas represented by the sensor signals.

74. A method of determining the consciousness of a person, the method comprising the steps of:

(A) mounting at least four facial muscle activity sensors so that each activity sensor generates an activity signal based on the level of activity of a different facial muscle group on the person;

(B) processing said activity signals to generate a first output signal based on the summation of the activity signals for the sensed facial muscle groups; and also including as step (C): stimulating a nerve in at least one of the sensed facial muscle groups and determining the level of paralysis from the muscle activity sensed by a facial muscle sensor.

75. The consciousness determining method of claim 74 also including as step (D): calibrating the first output signal based on the paralysis level determined in step (C).

76. The consciousness determining method of claim 74 also including as step (D): reporting to a monitor the paralysis level determined in step (C).

77. The consciousness determining method of claim 75 also including as step (E): reporting to a monitor the paralysis level determined in step (C) and the first output signal as calibrated in step (D).

78. The consciousness determining method of claim 75 wherein in step (B): processing said activity signals to generate a second output signal based on the differences between the activity signals for the sensed facial muscle groups.

79. The consciousness determining method of claim 76 also including in step (B): processing said activity signals to generate a second output signal based on the differences between the activity signals for the sensed facial muscle groups.

80. The consciousness determining method of claim 77 also including in step (B): processing said activity signals to generate a second output signal based on the differences between the activity signals for the sensed facial muscle groups; and including in step (E) also reporting the second output signal to the monitor in order to provide an indicator of the consciousness the person.

81. The consciousness determining method of claim 78 also including as step (E): reporting the first and second output signals and paralysis level to a monitor in order to provide an indicator of the consciousness the person.

82. The consciousness determining method of claim 79 also including as step (E): reporting the first and second output signals to a monitor in order to provide an indicator of the consciousness the person.

83. The consciousness determining method of claim 77 also including in step B: filtering the activity signals to remove from the first output signal an artifact representing muscle activity caused by stimulus to the person not indicative of the person's consciousness.

84. The consciousness determining method of claim 80 also including in step B: filtering the activity signals to remove from at least one output signal an artifact representing muscle activity caused by stimulus to the person not indicative of the person's consciousness.

85. The consciousness determining method of claim 82 also including in step B: filtering the activity signals to remove from at least one output signal an artifact representing muscle activity caused by stimulus to the person not indicative of the person's consciousness.

86. The consciousness determining method of claim 75 wherein, in step A, the four facial muscle areas are selected from among the frontalis area, the corrugator area, the zygomatic area, the masseter area, and the orbicularis oculi area.

87. The consciousness determining method of claim 83 wherein, in step A, the four facial muscle areas are selected from among the frontalis area, the corrugator area, the zygomatic area, the masseter area, and the orbicularis oculi area.

88. The consciousness determining method of claim 85 wherein, in step A, the four facial muscle areas are selected from among the frontalis area, the corrugator area, the zygomatic area, the masseter area, and the orbicularis oculi area.

89. The consciousness determining method of claim 75 wherein, in step A, five facial muscle activity sensors are mounted, respectively, on the following five muscle areas: the frontalis area, the corrugator area, the zygomatic area, the masseter area, and the orbicularis oculi area.

90. The consciousness determining method of claim 83 wherein, in step A, five facial muscle activity sensors are mounted, respectively, on the following five muscle areas: the frontalis area, the corrugator area, the zygomatic area, the masseter area, and the orbicularis oculi area.

91. The consciousness determining method of claim 85 wherein, in step A, five facial muscle activity sensors are mounted, respectively, on the following five muscle areas: the frontalis area, the corrugator area, the zygomatic area, the masseter area, and the orbicularis oculi area.

92. A method of determining the consciousness of a person, the method comprising the steps of:
(A) mounting at least four facial muscle activity sensors so that each activity sensor generates an activity signal based on the level of activity of a different facial muscle group on the person;
(B) processing said activity signals to generate a first output signal based on the summation of the activity signals for the sensed facial muscle groups: and
wherein, in step (A), five facial muscle activity sensors are mounted, respectively, on the following five muscle areas: the frontalis area, the corrugator area, the zygomatic area, the masseter area, and the orbicularis oculi area.

93. A method of determining the consciousness of a person, the method comprising the steps of:
(A) mounting at least four facial muscle activity sensors so that each activity sensor generates an activity signal based on the level of activity of a different facial muscle group on the person;
(B) processing said activity signals to generate a first output signal based on the summation of the activity signals for the sensed facial muscle groups;
also including as step (C): reporting the first and second output signals to a monitor in order to provide an indicator of the consciousness the person; and
wherein, in step (A), five facial muscle activity sensors are mounted, respectively, on the following five muscle areas: the frontalis area, the corrugator area, the zygomatic area, the masseter area, and the orbicularis oculi area.

94. A method of determining the consciousness of a person, the method comprising the steps of:
(A) mounting at least four facial muscle activity sensors so that each activity sensor generates an activity signal based on the level of activity of a different facial muscle group on the person;
(B) processing said activity signals to generate a first output signal based on the summation of the activity signals for the sensed facial muscle groups; also including in step (B): filtering the activity signals to remove from the first output signal an artifact representing muscle activity caused by stimulus to the person not indicative of the person's consciousness; and
wherein, in step (A), five facial muscle activity sensors are mounted, respectively, on the following five muscle areas: the frontalis area, the corrugator area, the zygomatic area, the masseter area, and the orbicularis oculi area.

95. An apparatus for indicating the consciousness of a person, comprising, in combination:
an array of facial muscle sensors adapted to generate sensor signals representing the simultaneous activity of at least four different facial muscle areas, each of which elicit distinctive patterns of facial expressions of the person;
a sensor signal processor operatively coupled to the sensors to receive the sensor signals from the facial muscle sensors and, based on the sensor signals, automatically generate an output signal indicating the consciousness of the person;
a facial muscle stimulator adapted to activate a facial nerve in at least one of said facial muscle areas; and
a facial nerve processor adapted to (a) receive sensor signals from the facial muscles sensors in said nerve-activated facial muscle area, (b) determine a paralysis level for said nerve-activated facial muscle area, and (c) adjust the sensor signal processor's generation of at least a portion of the output signal according to the determined paralysis level, whereby the output signal indicates the consciousness of the person despite partial paralysis of the nerve-activated facial muscle area.

96. An apparatus for indicating the consciousness of a person, comprising, in combination:
an array of facial muscle sensors adapted to generate sensor signals representing the simultaneous activity of at least four different facial muscle areas, each of which elicit distinctive patterns of facial expressions of the person;
a sensor signal processor operatively coupled to the sensors to receive the sensor signals from the facial muscle sensors and, based on the sensor signals, automatically generate an output signal indicating the consciousness of the person; and
in which the array of facial muscle sensors is also adapted to generate sensor signals representing the simultaneous activity of a fifth different facial muscle area.

97. An apparatus for indicating the consciousness of a person, comprising, in combination:
facial muscle sensor grouping, each adapted to generate a first sensor signal representing the activity of a first facial muscle area that elicits a first portion of the facial expression of the person;
a facial muscle stimulator adapted to activate a facial nerve in said first facial muscle area;
a processor apparatus operatively coupled to said each facial muscle sensor grouping to (i) receive at least the first sensor signal from a first facial muscle sensor grouping, (ii) determine a paralysis level for the facial muscle area based on the first sensor signal received subsequent to activation of the facial nerve by the facial muscle stimulator, and (iii) generate an output signal based on at least the first sensor signal and the determined paralysis level, whereby the output signal indicates the consciousness of the person despite partial paralysis of the nerve-activated first facial muscle area; and
the sensor signal processor generates at least a patterned portion of the output signal based on relative differences among the sensor signals and thereby the different activities of the different facial muscle areas represented by the sensor signals.

98. A method of determining the consciousness of a person, the method comprising the steps of:
- (A) mounting at least five facial muscle activity sensors so that each activity sensor generates an activity signal based on the level of activity of a different facial muscle group on the person;
- (B) processing said activity signals to generate a first output signal based on the summation of the activity signals for the sensed facial muscle groups; and
- wherein, in step (A), five facial muscle activity sensors are mounted, respectively, on the following five muscle areas: the frontalis area, the corrugator area, the zygomatic area, the masseter area, and the orbicularis oculi area.

99. The apparatus of claim 9 in which the array of facial muscle sensors is also adapted to generate sensor signals representing the simultaneous activity of a fifth different facial muscle area.

100. An apparatus for indicating the consciousness of a person, comprising in combination:
- an array of facial muscle sensors adapted to generate sensor signals representing the simultaneous activity of at least four different facial muscle areas, each of which elicit distinctive patterns of facial expressions of the person;
- a sensor signal processor operatively coupled to the sensors to receive the sensor signals from the facial muscle sensors and, based on the sensor signals, automatically generate an output signal indicating the consciousness of the person:
- wherein the facial muscle sensors are surface electromyograms adapted to be physically attached to the person's face in positions allowing the monitoring of the different facial muscles;
- wherein said facial muscle areas are selected from among the frontalis area, the corrugator area, the zygomatic area, the masseter area, and the orbilaris oculi area; and in which the array of facial muscle sensors is also adapted to generate sensor signals representing the simultaneous activity of a fifth different facial muscle area.

* * * * *